(12) United States Patent
Vegeto et al.

(10) Patent No.: US 6,599,698 B1
(45) Date of Patent: Jul. 29, 2003

(54) MUTATED STEROID HORMONE RECEPTORS, METHODS FOR THEIR USE AND MOLECULAR SWITCH FOR GENE THERAPY

(75) Inventors: Elisabetta Vegeto, Houston, TX (US); Donald P. McDonnell, San Diego, CA (US); Bert W. O'Malley, Houston, TX (US); William T. Schrader, San Diego, CA (US); Ming-Jer Tsai, Houston, TX (US)

(73) Assignee: Baylor College of Medicine, Houston, TX (US)

(*) Notice: Subject to any disclaimer, the term of this patent is extended or adjusted under 35 U.S.C. 154(b) by 0 days.

(21) Appl. No.: 09/209,981

(22) Filed: Dec. 9, 1998

Related U.S. Application Data

(60) Division of application No. 08/479,846, filed on Jun. 6, 1995, now Pat. No. 5,824,534, which is a continuation of application No. 07/939,246, filed on Sep. 2, 1992, now abandoned, which is a continuation-in-part of application No. 07/882,771, filed on May 14, 1992, now Pat. No. 5,364,791.

(51) Int. Cl.[7] .............................. C12Q 1/63; C12N 7/01; C12N 5/00; C07H 21/04
(52) U.S. Cl. .................... 435/6; 435/235.1; 435/325; 536/23.1
(58) Field of Search ..................... 435/6, 320.1, 325, 435/465; 536/24.1, 23.1

(56) References Cited

U.S. PATENT DOCUMENTS

| | | | |
|---|---|---|---|
| 4,736,866 A | | 4/1988 | Leder et al. |
| 4,981,784 A | | 1/1991 | Evans et al. |
| 5,071,773 A | * | 12/1991 | Evans et al. ............. 436/501 |
| 5,215,916 A | * | 6/1993 | Simons et al. ........... 435/252.3 |
| 5,283,173 A | | 2/1994 | Fields et al. |
| 5,310,662 A | * | 5/1994 | Evans et al. ............. 435/64.1 |
| 5,312,732 A | * | 5/1994 | Evans et al. ............. 435/69.1 |
| 5,364,791 A | | 11/1994 | Vegeto et al. |
| 5,571,696 A | * | 11/1996 | Evans et al. ............. 435/69.1 |
| 5,928,422 A | | 7/1999 | Uchiyama et al. |

FOREIGN PATENT DOCUMENTS

| | | | | |
|---|---|---|---|---|
| EP | 0 371 820 A | | 6/1990 | |
| WO | WO 90/06318 | * | 6/1990 | ............. 536/23.1 |
| WO | 90/07517 A | | 7/1990 | |
| WO | 90/14356 A | | 11/1990 | |
| WO | 92/22567 A | | 12/1992 | |
| WO | 93/18759 | | 9/1993 | |
| WO | 93/23431 | | 11/1993 | |
| WO | 96/40911 | | 12/1996 | |

OTHER PUBLICATIONS

Ruiz et al. Functional characterization of a natural retinoic acid responsive element. EMBO J. vol. 10(12):3829–2838, Nov. 26, 1991.*

Krishna et al. Repression of the human glycoprotein hormone alpha–subunit gene by glucocorticoids evidence for receptor interactions with limiting trasncriptional activators. Mol. Endocrinol. vol. 5(1):100–110, May 1991.*

Verma et al. Gene therapy—promises, problems and prospects. Nature. vol. 389:239–242, Sep. 18, 1997.*

Marshall, E. Gene therapy's growing pains. Science vol. 269:1050–1055, Aug. 25, 1995.*

Orkin et al. Report and recommendations of the panel to assess the NIH investment in research on gene therapy, Dec. 7, 1995.*

Anderson, WF. Human gene therapy. Nature. vol. 392:25–30, Apr. 30, 1998.*

Kellendonk, et al., "Regulation of Cre Recombinase Activity by the Synthetic Steroid RU486," *Nucleic Acids Research* 24(8):1404–1411 (1996).

Lanz, et al., "Active, Interactive, and Inactive Steroid Receptors Mutants," *Steroids* 59:148–152 (1994).

Laudet, "Les Recepteurs Nucleaires," *Pour La Science* 183:32–39 (1993).

Lewin, "Genes V," Oxford University Press, Oxford (1994).

Malchoff, et al., "A Mutation of the Glucocorticoid Receptor in Primary Cortisol Resistance," *Journal of Clinical Investigation* 91(5):1918–1925 (1993).

Veldscholte, et al., "Anti–Androgens and the Mutated Androgen Receptor of LNCap Cells: Differential Effects on Binding Affinity, Heat–Shock Protein Interaction, and Transription Activation," *Biochemistry* 32:2393–2399 (1992).

Wurtz, et al., "A Canonical Structure for the Ligand–Binding Domain of Nuclear Receptors," *Natural Structural Biology* 3:87–94 (1996).

Akerblom et al., "Negative Regulation by Glucocorticoids Through Interference with a cAMP Responsive Enhancer," *Science* 241:350–353 (1988).

Allan et al., "Hormone and Antihormone Induce Distant Conformational Changes Which Are Central to Steroid Receptor Activation," *J. Biol. Chem.* 267:19513–19520 (1992).

(List continued on next page.)

*Primary Examiner*—Remy Yucel
*Assistant Examiner*—William Sandals
(74) *Attorney, Agent, or Firm*—Perkins Coie LLP; Michael J. Wise

(57) ABSTRACT

The present invention provides mutant proteins of steroid hormone receptors. These mutant proteins are useful in methods of distinguishing a steroid hormone receptor antagonist from a steroid hormone receptor agonist. The present invention also provides plasmids containing mutated steroid hormone receptor proteins and cells transfected with those plasmids. In addition, the present invention provides methods for determining whether a compound is a steroid hormone receptor antagonist or agonist. Also, the present invention provides methods of determining endogenous ligands for steroid hormone receptors. The invention further provides a molecular switch for regulating expression in gene therapy and methods of employing the molecular switch in humans, animals, transgenic animals and plants.

32 Claims, 9 Drawing Sheets

OTHER PUBLICATIONS

Allan et al., "Ligand–dependent conformational changes in the progesterone receptor are necessary for events that follow DNA binding," *Proc. Natl. Acad. Sci. USA* 89:11750–11754 (1992).

Barzel, "Estrogens in the Prevention and Treatment of Postmenopausal Osteoporosis: A review," *American Journal of Medicine* 85:847–850 (1988).

Beato, "Gene Regulation by Steroid Hormones," *Cell* 56:335–344 (1989).

Beato, "Transcriptional control by nuclear receptors," *FASEB J.* 5:2044–2051 (1991).

Beekman et al., "Transcriptional Activation by the Estrogen Receptor Requires a Conformational Change in the Ligand Binding Domain," *Molecular Endocrinology* 7:1266–1274 (1993).

Berry et al., "Role of the two activating domains of the oestrogen receptor in the cell–type and promoter–context dependent agonistic activity of the anti–oestrogen 4–hydroxytamoxifen," *EMBO J.* 9:2811–2818 (1990).

Braselmann et al., "A selective transcriptional induction system for mammalian cells based on Gal4–estrogen receptor fusion proteins," *Proc. Natl. Acad. Sci. USA* 90:1657–1661 (1993).

Cato et al., "Steroids and Growth Promoting Factors in the Regulation of Expression of Genes and Gene Networks," *J. Steroid Biochem. Molec. Biol.* 43:63–68 (1992).

Celada et al., "Repression of Major Histocompatibility Complex IA Expression by Glucocorticoids: The Glucocorticoid Receptor Inhibits the DNA Binding of the X Box DNA Binding Protein," *J. Exp. Med.* 1.77:691–698 (1993).

Chu et al., "Efficiency of Cytoplasmic Delivery by pH–Sensitive Liposomes to Cells in Culture," *Pharmaceutical Research* 7:824–834 (1990).

Curiel et al., "Gene Transfer to Respiratory Epithelial Cells via the Receptor–mediated Endocytosis Pathway," *Am. J. Respir. Cell Mol. Biol.* 6:247–252 (1992).

Dahlman–Wright et al., "Interaction of the Glucocorticoid Receptor DNA–binding Domain with DNA as a Dimer Is Mediated by a Short Segment of Five Amino Acids," *J. Biol. Chem.* 266:3107–3112 (1991).

Daneshgari et al., "Endocrine Therapy of Advanced Carcinoma of the Prostate," *Cancer* 71:1089–1097 (1993).

Denis et al., "Requirement of hormone for thermal conversion of the glucocorticoid receptor to a DNA–binding state," *Nature* 333:686–688 (1988).

Denis et al., "The Molybdate–stabilized Nonactivated Glucocorticoid Receptor Contains a Dimer of $M_r$ 90,000 Non–hormone–binding Protein," *J. Biol. Chem.* 262:11803–11806 (1987).

Diamond et al., "Transcriptional Factor Interactions: Selectors of Positive or Negative Regulation from a Single DNA Element," *Science* 249:1266–1272 (1990).

Dobson et al., "Mutational Analysis of the Chicken Progesterone Receptor," *J. Biol. Chem.* 264:4207–4211 (1989).

Dreicer and Wilding, "Steroid Hormone Agonists and Antagonists in the Treatment of Cancer," *Cancer Investigation* 10:27–41 (1992).

Drouin et al., "Glucocorticoid Receptor Binding to a Specific DNA Sequence is Required for Hormone–Dependent Repression of Pro–Opiomelanocortin Gene Transcription," *Molecular and Cellular Biology* 9:5305–5314 (1989).

Elliston et al., "Superactive Estrogen Receptors," *J. Biol. Chem.* 265(20):11517–11521 (1990).

Evans, "The Steroid and Thyroid Hormone Receptor Superfamily," *Science* 240:889–895 (1988).

Fuller et al., "The steroid receptor superfamily: mechanisms of diversity," *FASEB J.* 5:3092–3099 (1991).

Gauthier et al., "Functional interference between the Spi–1/Pu.1 oncoprotein and steroid hormone or vitamin receptors," *EMBO J.* 12:5089–5096 (1993).

Gronemeyer et al., "Mechanisms of Hormone Action," *J. Steroid Biochem. Molec. Biol.* 41(3–8):217–221 (1992).

Haensler and Szoka, "Synthesis and Characterization of a Trigalactosylated Bisacridine Compound to Target DNA to Hepatocytes," *Bioconjugate Chem.* 4:85–93 (1993).

Heck et al., "A distinct modulating domain in glucocorticoid receptor monomers in the repression of activity of the transcription factor AP–1," *EMBO J.* 13:4087–4095 (1994).

Hollenberg and Evans, "Multiple and Cooperative Trans–Activation Domains of the Human Glucocorticoid Receptor," *Cell* 55:899–906 (1988).

Howard and Distelhorst, "Evidence for Intracellular Association of the Glucocorticoid Receptor with the 90–kDa Heat Shock Protein," *J. Biol. Chem.* 263:3474–3481 (1988).

Ito et al., "Transformation of Intact Yeast Cells Treated with Alkali Cations," *J. Bacteriol.* 153:163–168 (1983).

Jonat et al., "Antitumor Promotion and Antiinflammation: Down–Modulation of AP–1 (Fos/Jun) Activity by Glucocorticoid Hormone," *Cell* 62:1189–1204 (1990).

Kawai and Nishizawa et al., "New Procedure for DNA Transfection with Polycation and Dimethyl Sulfoxide," *Molecular and Cellular Biology* 4:1172–1174 (1984).

Kerppola et al., "Fos is a Preferential Target of Glucocorticoid Receptor Inhibition of AP–1 Activity In Vitro," *Molecular and Cellular Biology* 13:3782–3791 (1993).

Kutoh et al., "Functional Inteference between the Ubiquitous and Constitutive Octamer Transcription Factor 1 (OTF–1) and the Glucocorticoid Receptor by Direct Protein—Protein Interaction Involving the Homeo Subdomain of OTF–1," *Molecular and Cellular Biology* 12:4960–4969 (1992).

Lanz and Rusconi, "A Conserved Carboxy–Terminal Subdomain Is Important for Ligand Interpretation and Transactivation by Nuclear Receptors," *Endocrinology* 135:2183–2195 (1994).

Lebeau et al., "P59, an hsp 90–binding Protein," *J. Biol. Chem.* 267:4281–4284 (1992).

Legendre and Szoka, "Cyclic Amphipathic Peptide–DNA Complexes Mediate High–efficiency Transfection of Adherent Mammalian Cells," *Proc. Natl. Acad. Sci. USA* 90:893–897 (1993).

Legendre and Szoka, "Delivery of Plasmid DNA into Mammalian Cell Lines Using pH–Sensitive Liposomes: Comparison with Cationic Liposomes," *Pharmaceutical Research* 9:1235–1242 (1992).

Lerner et al., "Isolation of Subtilisin Pro–sequence Mutations that Affect Formation of Active Protease by Localized Random Polymerase Chain Reaction Mutagenesis," *J. Biol. Chem.* 265:20085–20086 (1990).

Liu et al., "Hormone–Independent Repression of AP–1–Inducible Collagenase Promoter Activity by Glucocorticoid Receptors," *Molecular and Cellular Biology* 15:1005–1013 (1995).

Lucibello et al.,. "Mutational transrepression of Fos and the glucocorticoid receptor: involvement of a functional domain in Fos which is absent in FosB," *EMBO J.* 9:2827–2834 (1990).

Mak et al., "Expression of Functional Chicken Oviduct Progesterone Receptors in Yeast (*Saccharomyces cerevisiae*)," *J. Biol. Chem.* 264:21613–21618 (1989).

McDonnell et al., "Reconstitution of the Vitamin D–Responsive Osteocalcin Transcription Unit in *Saccharomyces cerevisiae*," *Molecular and Cellular Biology* 9:3517–3523 (1989).

Mendel et al., "Molybdate–stabilized Nonactivated Glucocorticoid–Receptor Complexes Contain a 90–kDa Non–steroid–binding Phosphoprotein That is Lost on Activation," *J. Biol. Chem.* 261:3758–3763 (1986).

Meyer et al., "Agonistic and antagonistic activities of RU486 on the functions of the human progesterone receptor," *EMBO J.* 9:3923–3932 (1990).

Miller, "Assay of –Galactosidase," *Experiments in Molecular Genetics*, Cold Spring Harbor Laboratories, pp. 352–355 (1972).

Miner et al., "Joints in the Regulatory Lattice: Composite Regulation by Steroid Receptor–AP1 Complexes," *Cell Growth & Differentiation* 2:525–530 (1991).

Misrahi et al., "Complete Amino Acid Sequence of the Human Progesterone Receptor Deduced from Cloned cDNA," *Biochemical and Biophysical Research Communications* 143:740–748 (1987).

Mordacq and Linzer, "Co–localization of elements required for phorbol ester stimulation and glucocorticoid repression of proliferin gene expression," *Genes & Development* 3:760–769 (1989).

Nagaya et al., "Thyroid Hormone Receptor Mutants That Cause Resistance to Thyroid Hormone: Evidence For Receptor Competition for DNA Sequences in Target Genes," *J. Biol. Chem.* 267:13014–13019 (1992).

O'Malley and Tsai, "Molecular Pathways of Steroid Receptor Action," *Biology of Reproduction* 46:163–167 (1992).

Oro et al., "Transcriptional Inhibition by a Glucocorticoid Receptor—Ga 1 actosidase Fusion Protein," *Cell* 65:1109–1114 (1988).

Palmiter and Brinster, "Germ–line Transformation of Mice," *Ann. Rev. Genet.* 20:465–499 (1986).

Pfahl, "Nuclear Receptor/AP–1 Interaction," *Endocrine Reviews* 14:651–658 (1993).

Pham et al., "Antiestrogen can Establish Nonreproductive Receptor Complexes and Alter Chromatin Structure at Target Enhancers," *PNAS USA* 88:3125–3129 (1991).

Picard et al., "Signal transduction by steroid hormones: nuclear localization is differentially regulated in estrogen and glucocorticoid receptors," *Cell Regulation* 1:291–299 (1990).

Pratt et al., "The hsp56 Immunophilin Component of Steroid Receptor Heterocomplexes: Could This be the Elusive Nuclear Localization Signal–Binding Protein?" *J. Steroid Biochem. Molec. Biol.* 3:269–279 (1993).

Rao and Slotman, "Endocrine Factors in Common Epithelial Ovarian Cancer," *Endocrine Reviews* 12:14–26 (1991).

Ray and Prefontaine, "Physical association and functional antagonism between the p65 subunit of transcription factor NF–$_\kappa$B and the glucocorticoid receptor," *Proc. Natl. Acad. Sci. USA* 91:752–756 (1994).

Rexin et al., "Structure of the Glucocorticoid Receptor in Intact Cells in the Absence of Hormone," *J. Biol. Chem.* 267:9619–9621 (1992).

Sanchez et al., "Evidence that the 90–kDa Phosphoprotein Associated with the Untransformed L–cell Glucocorticoid Receptor is a Murine Heat Shock Protein," *J. Biol. Chem.* 260:12398–12401 (1985).

Sanchez et al., "Hormone–free Mouse Glucocorticoid Receptors Overexpressed in Chinese Hamster Ovary Cells Are Localized in the Nucleus and Are Associated with Bolth hsp70 and hsp90," *J. Biol. Chem.* 265:20123–20130 (1990).

Sanchez et al., "Relationship of the 90–kDa Murine Heat Shock Protein to the Untransformed and Transformed States of the L Cell Glucocorticoid Receptor," *J. Biol. Chem.* 262:6986–6991 (1987).

Sanchez, "Hsp56: A Novel Heat Shock Protein Associated with Untransformed Steroid Receptor Complexes," *J. Biol. Chem.* 265:22067–22070 (1990).

Schule and Evans, "Cross–coupling of signal transduction pathways: zinc finger meets leucine zipper," *Trends in Genetics* 7:377–381 (1991).

Schule et al., "Functional Antagonism between Oncoprotein c–Jun and the Glucocorticoid Receptor," *Gene* 62:1217–1226 (1990).

Seed and Sheen, "A simple phase–extraction assay for chloramphenicol acyltransferase activity," *Gene* 67:271–277 (1988).

Smith and Toft, "Steroid Receptors and Their Associated Proteins," *Molecular Endocrinology* 7:4–11 (1993).

Stromstedt et al., "The Glucocorticoid Receptor Binds to a Sequence Overlapping the TATA Box of the Human Osteocalcin Promoter: a Potential Mechanism for Negative Regulation," *Molecular and Cellular Biology* 11:3379–3383 (1991).

Sunderland and Osborne, "Tamoxifen in Premenopausal Patients with Metastatic Breast Cancer: A Review," *J. Clinical Oncology* 9:1283–1297 (1991).

Touray et al., "Characteristics of functional inhibition of the glucocorticoid receptor by Fos/Jun," *Oncogene* 6:1227–1234 (1991).

Tsai et al., "Cooperative Binding of Steroid Hormone Receptors Contributes to Transcriptional Synergism at Target Enhancer Elements," *Cell* 57:443–448 (1989).

Tsai et al., "Molecular Interactions of Steroid Hormone Receptor with its Enhancer Element: Evidence for Receptor Dimer Formation," *Cell* 55:361–369 (1988).

Tverberg and Russo, "Cell–specific Glucocorticoid Repression of Calcitonin/Calcitonin Gene–related Peptide Transcription," *J. Biol. Chem.* 267:17567–17573 (1992).

Uhlen and Moks, "Gene Fusions for Purpose of Expression: An Introduction," *Methods in Enzymology* 185:129–143 (1990).

Umesono and Evans, "Determinants of Target Gene Specificity for Steroid/Thyroid Hormone Receptors," *Cell* 57:1139–1146 (1989).

Vegeto et al., "The Mechanism of RU486 Antagonism Is Dependent on the Conformation of the Carboxy–Terminal Tail of the Human Progesterone Receptor," *Cell* 69:703–713 (1992).

Wagner et al., "Transferrin–polycation–DNA complexes: The effect of polycations on the structure of the complex and DNA delivery into cells," *Proc. Natl. Acad. Sci. USA* 88:4255–4259 (1991).

Ward, "Single–step purification of shuttle vectors from yeast for high frequency back–transformation into *E. coli,*" *Nucleic Acid Research* 18:5319 (1990).

Webster et al., "The Hormone–Binding Domains of the Estrogen and Glucocorticoid Receptors Containing an Inducible Transcription Activation Function," *Cell* 54:199–207 (1988).

Yang–Yen et al., "Transcription Interference between c–Jun and the Glucocorticoid Receptor: Mutual Inhibition of DNA Binding Due to Direct Protein—Protein Interaction," *Cell* 62:1205–1215 (1990).

Yem et al., "The Hsp56 Component of Steroid Receptor Complexes Binds to Immobilized FK506 and Shows Homology to FKBP–12 and FKBP–13," *J. Biol. Chem.* 267:2868–2871 (1992).

* cited by examiner

B

DNA sequence:

```
       2636
WT  ..AAC TTG CAT GAT CTT GTC AAA CAA CTT CAT CTG TAC TGC TTG..
UP-1..AAT TGC ATG ATC TTG TCA AAC AAC TTC ATC TGT ACT GCT TGA
```

Protein sequence:

```
       879                                               891
WT  ..Asn Leu His Asp Leu Val Lys Gln Leu His Leu Tyr Cys Leu..
                             *   *
UP-1..Asn Cys Met Ile Leu Ser Asn Asn Phe Ile Cys Thr Ala
```

| hPR Constructs | Transcriptional Activity (Miller Units) | | | Specific Binding (nM) | |
| --- | --- | --- | --- | --- | --- |
| | − | P | RU | P | RU |
| YEphPR-B (933) | 86 | 6200 | 586 | 1.0 | 1.3 |
| UP-1 | 286 | 466 | 8050 | 0.02 | 1.6 |
| YEphPR-B879 | 166 | 242 | 5900 | 0.04 | 1.8 |
| YEphPR-B891 | 243 | 226 | 6175 | 0.03 | 1.6 |

Fig.4

MUTATED STEROID HORMONE RECEPTORS, METHODS FOR THEIR USE AND MOLECULAR SWITCH FOR GENE THERAPY

This application is a divisional of U.S. patent application Ser. No. 08/479,846, filed Jun. 6, 1995, now U.S. Pat. No. 5,874,534, Vegeto et al., issued Feb. 23, 1999, entitled "MUTATED STEROID HORMONE RECEPTORS, METHODS FOR THEIR USE AND MOLECULAR SWITCH FOR GENE THERAPY", which is a continuation of U.S. patent application Ser. No. 07/939,246, Vegeto et al., filed Sep. 2, 1992, entitled "entitled "MUTATED STEROID HORMONE RECEPTORS, METHODS FOR THEIR USE AND MOLECULAR SWITCH FOR GENE THERAPY", now abandoned, which is a continuation-in-part of U.S. patent application Ser. No. 07/882,771, filed May 14, 1992, now U.S. Pat. No. 5,364,791, entitled "PROGESTERONE RECEPTOR HAVING C TERMINAL HORMONE BINDING DOMAIN TRUNCATIONS".

This invention was supported in part through a grant or award from the National Institute of Health.

BACKGROUND OF THE INVENTION

1. Field of the Invention

The present invention relates generally to the fields of molecular endocrinology and receptor pharmacology. It further relates to molecular switches for gene therapy. More specifically, the present invention relates to a novel in vivo method for the identification of steroid hormone receptor agonists and antagonists and to a molecular switch involving a modified steroid receptor for up-regulating and down-regulating the synthesis of heterologous nucleic acid sequences which have been inserted into cells.

2. Description of the Related Art

Steroid receptors are responsible for the regulation of complex cellular events, including transcription. The ovarian hormones, estrogen and progesterone, are responsible, in part, for the regulation of the complex cellular events associated with differentiation, growth and functioning of female reproductive tissues. These hormones play also important roles in development and progression of malignancies of the reproductive endocrine system.

The biological activity of steroid hormones is mediated directly by a hormone and tissue-specific intracellular receptor. The physiologically inactive form of the receptor may exist as an oligomeric complex with proteins, such as heat-shock protein (hsp) 90, hsp70 and hsp56. Upon binding its cognate ligand, the receptor changes conformation and dissociates from the inhibitory heteroligomeric complex. Subsequent dimerization allows the receptor to bind to specific DNA sites in the regulatory region of target gene promoters. Following binding of the receptor to DNA, the hormone is responsible for mediating a second function that allows the receptor to interact specifically with the transcription apparatus. Displacement of additional inhibitory proteins and DNA-dependent phosphorylation may constitute the final steps in this activation pathway.

Cloning of several members of the steroid receptor superfamily has facilitated the reconstitution of hormone-dependent transcription in heterologous cell systems. Subsequently, in vivo and in vitro studies with mutant and chimeric receptors have demonstrated that steroid hormone receptors are modular proteins organized into structurally and functionally defined domains. A well defined 66 amino acid DNA binding domain (DBD) has been identified and studied in detail, using both genetic and biochemical approaches. The ligand (hormone) binding domain (LBD), located in the carboxyl-terminal half of the receptor, consists of about 300 amino acids. It has not been amenable to detailed site-directed mutagenesis, since this domain appears to fold into a complex tertiary structure, creating a specific hydrophobic pocket which surrounds the effector molecule. This feature creates difficulty in distinguishing among amino acid residues that affect the overall structure of this domain from those involved in a direct contact with the ligand. The LBD also contains sequences responsible for receptor dimerization, hsp interactions and one of the two transactivation sequences of the receptor.

Gene replacement therapy requires the ability to control the level of expression of transfected genes from outside the body. Such a "molecular switch" should allow specificity, selectivity, precision safety and rapid clearance. The steroid receptor family of gene regulatory proteins is an ideal set of such molecules. These proteins are ligand activated transcription factors whose ligands can range from steroids to retinoids, fatty acids, vitamins, thyroid hormones and other presently unidentified small molecules. These compounds bind to receptors and either up-regulate or down-regulate. The compounds are cleared from the body by existing mechanisms and the compounds are non-toxic.

The efficacy of a ligand is a consequence of its interaction with the receptor. This interaction can involve contacts causing the receptor to become active (agonist) or for the receptor to be inactive (antagonist). The affinity of antagonist activated receptors for DNA is similar to that of agonist-bound receptor. Nevertheless, in the presence of the antagonist, the receptor cannot activate transcription efficiently. Thus, both up and down regulation is possible by this pathway.

The present invention shows that receptors can be modified to allow them to bind various ligands whose structure differs dramatically from the naturally occurring ligands. Small C-terminal alternations in amino acid sequence, including truncation, result in altered affinity and altered function of the ligand. By screening receptor mutants, receptors can be customized to respond to ligands which do not activate the host cells own receptors. Thus regulation of a desired transgene can be achieved using a ligand which will bind to and regulate a customized receptor.

Steroid receptors and other mammalian transcription regulators can function in yeast. This fact, coupled with the ease of genetic manipulation of yeast make it a useful system to study the mechanism of steroid hormone action.

A long felt need and desire in this art would be met by the development of methods to identify steroid hormone receptors agonists and antagonists. The development of such a method will facilitate the identification of novel therapeutic pharmaceuticals. Additionally, the present invention provides a novel approach to regulate transcription in gene therapy. By using modified steroid receptors and custom ligands, up-regulation and down-regulation of inserted nucleic acid sequences can be achieved.

SUMMARY OF THE INVENTION

An object of the present invention is a modified steroid hormone receptor protein for distinguishing hormone antagonists and agonists.

An additional object of the present invention is a plasmid containing a modified hormone receptor.

A further object of the present invention are transfected cells containing modified hormone receptors.

Another object of the present invention is a transformed cell containing modified hormone receptors.

An additional object of the present invention is a method for determining agonist activity of a compound for steroid hormone receptors.

A further object of the present invention is a method for determining antagonist activity of a compound for steroid hormone receptors.

An object of the present invention is a method for determining endogenous ligands for steroid hormone receptors.

An object of the present invention is an endogenous ligand for a modified steroid receptor.

An object of the present invention is a molecular switch for regulated expression of a nucleic acid sequence in gene therapy.

An additional object of the present invention is a molecular switch which binds non-natural ligands, anti-hormones and non-native ligands.

A further object of the present invention is a molecular switch comprised of a modified steroid receptor.

An additional object of the present invention is a method for regulating expression of nucleic acid sequence in gene therapy.

A further object of the present invention is a modified progesterone receptor with a native binding domain replaced with GAL-4 DNA.

An additional object of the present invention is to add a more potent activation domain to the receptor.

Another object of the present invention is a method of treating senile dementia or Parkinson's disease.

Thus, in accomplishing the foregoing objects, there is provided in accordance with one aspect of the present invention a mutated steroid hormone receptor protein. This mutated steroid hormone receptor protein is capable of distinguishing a steroid hormone receptor antagonist from a steroid hormone receptor agonist.

In specific embodiments of the present invention, the receptor is selected from a group consisting of estrogen, progesterone, androgen, Vitamin D, COUP-TF, cis-retonic acid, Nurr-1, thyroid hormone, mineralocorticoid, glucocorticoid-α, glucocorticoid-β, ecdysterone and orphan receptors.

In a preferred embodiment the mutated steroid receptor is mutated by deletion of carboxy terminal amino acids. Deletion usually comprises from one to about 120 amino acids and is most preferably less than about 60 amino acids.

In another embodiment of the present invention, there is provided a plasmid containing a mutated steroid hormone receptor protein. The plasmid of the present invention when transfected into a cell, is useful in determining the relative antagonist or agonist activity of a compound for a steroid hormone receptor.

In another embodiment of the present invention, there is provided transfected and transformed cells containing a plasmid in which a mutated or steroid hormone receptor protein has been inserted. The transfected cells of the present invention are useful in methods of determining the activity of a compound for a steroid hormone receptor.

Another embodiment of the present invention, includes methods of determining whether a compound has activity as an agonist or antagonist as a steroid hormone receptor. These methods comprise contacting the compound of interest with the transfected cells of the present invention and measuring the transcription levels induced by the compound to determine the relative agonist or antagonist activity of the steroid hormone receptors.

In other embodiments of the present invention, there is provided a method of determining an endogenous ligand for a steroid hormone receptor. This method comprises contacting a compound with the transfected cells of the present invention and measuring the transcription levels induced by the compound.

Another embodiment of the present invention is the provision of endogenous ligands for modified steroid hormone receptors that are capable of stimulating transcription in the presence of the transfected cells of the present invention.

A further embodiment of the present invention is a molecular switch for regulating expression of a nucleic acid sequence in gene therapy in humans and animals. It is also useful as a molecular switch in plants and in transgenic animals. The molecular switch is comprised of a modified steroid receptor which includes a natural steroid receptor DNA binding domain attached to a modified ligand binding domain on said receptor.

In specific embodiments of the molecular switch, the native DNA binding domain in unmodified form is used and the ligand binding domain is modified to only bind a compound selected from the group consisting of non-natural ligands, anti-hormones and non-native ligands.

Specific examples of compounds which bind the ligand binding domain include 5-alpha-pregnane-3,20-dione; 11β-(4-dimethylaminophenyl)-17β-hydroxy-17α-propinyl-4,9-estradiene-3-one; 11β-(4-dimethylaminophenyl)-17α-hydroxy-17β-(3-hydroxypropyl)-13α-methyl-4,9-gonadiene-3-one; 11β-(4-acetylphenyl)-17β-hydroxy-17α-(1-propinyl)-4,9-estradiene-3-one; 11β-(4-dimethylaminophenyl)-17β-hydroxy-17α-(3-hydroxy-1(Z)-propenyl-estra-4,9-diene-3-one; (7β,11β,17β)-11-(4-dimethylaminophenyl)-7-methyl-4',5'-dihydrospiro(ester-4,9-diene-17,2'(3'H)-furan)-3-one; (11β,14β,17α)-4'5'-dihydro-11-(4-dimethylaminophenyl)-(spiroestra-4,9-diene-17,2'(3'H)-furan)-3-one.

In preferred embodiments of the molecular switch, the modified steroid receptor has both the ligand binding domain and DNA binding domain replaced. For example the natural DNA binding domain is replaced with a DNA binding domain selected from the group consisting of GAL-4 DNA, virus DNA binding site, insect DNA binding site and a non-mammalian DNA binding site.

In specific embodiments of the present invention the molecular switch can further include transactivation domains selected from the group consisting of VP-16, TAF-1, TAF-2, TAU-1 and TAU-2.

In a preferred embodiment the molecular switch has a modified progesterone receptor containing a modified ligand binding domain and a GAL-4 DNA binding domain. This molecular switch can also be enhanced by the addition of a TAF-1 or VP16 transactivation domain.

Additional embodiments of the present invention include a method for regulating the expression of a nucleic acid cassette in gene therapy. The method includes the step of attaching the molecular switch to a nucleic acid cassette used in gene therapy. A sufficient dose of the nucleic acid cassette with the attached molecular switch is then be introduced into an animal or human to be treated. The molecular switch can then be up-regulated or down-regulated by dosing the animal or human with a ligand which binds the modified binding site.

Other and further objects, features and advantages will be apparent from the following description of the presently preferred embodiments of the invention which are given for the purposes of disclosure when taken in conjunction with the accompanying drawings.

BRIEF DESCRIPTION OF THE DRAWINGS

FIG. 4 shows the transcriptional activity and hormone binding analysis of wild type and mutant human progesterone receptor constructs.

Figure 1:
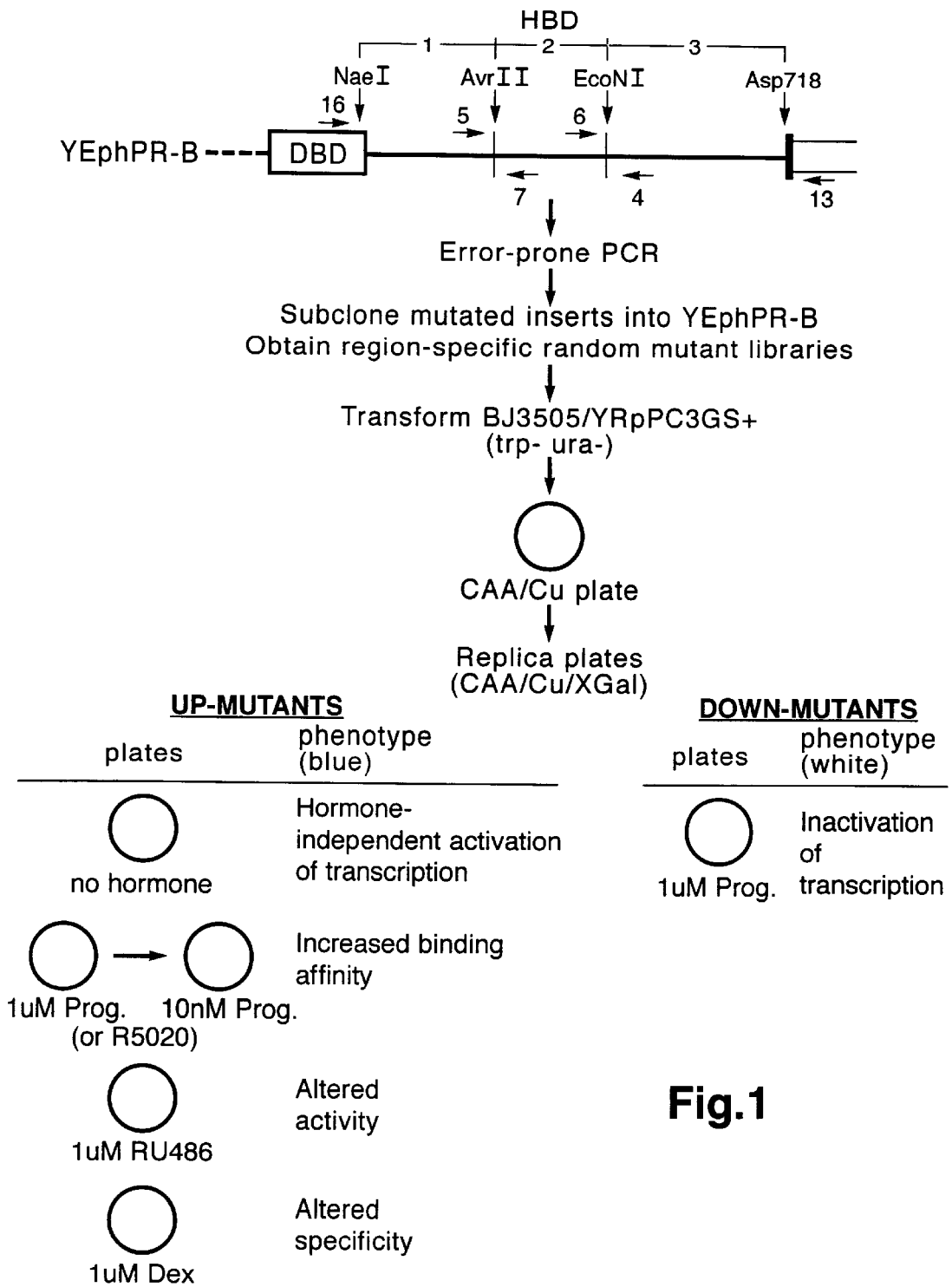
FIG. 1 shows the mutagenesis and screening strategy used in the present experiments.

The drawings are not necessarily to scale. Certain features of the invention may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and spirit of the invention.

Definitions

The term "steroid hormone receptor superfamily" as used herein refers to the superfamily of steroid receptors, some of which are known steroid receptors whose primary sequence suggests that they are related to each other. Representative examples of such receptors include the estrogen, progesterone, glucocorticoid-α, glucocorticoid-β, mineralocorticoid, androgen, thyroid hormone, retinoic acid, retinoid X, Vitamin D, COUP-TF, ecdysone, Nurr-1 and orphan receptors.

Receptors are composed of a DNA binding domain and a ligand binding domain. The DNA binding domain contains the receptor regulating sequence and binds DNA and the ligand binding domain binds the specific biological compound (ligand) to activate the receptor.

The term "orphan receptors" as used herein refers to a family of approximately twenty receptors whose primary amino acid sequence is closely related to the primary amino acid sequence of the steroid hormone receptor. They are called orphan receptors because no ligand has been identified which directly activates any of the members of this family.

"A and B forms of the progesterone receptor" are two distinct forms of the progesterone receptor that are derived from the same gene. The process for generation of the products may be alternate initiation of transcription, splicing differences or may relate to the promotor structure.

"Estrogen response element" is a synthetic or naturally occurring DNA sequence which, when placed into a heterologous promotor can confer estrogen responsiveness to that promotor in the presence of estrogen activated estrogen receptor.

The term "ligand" refers to any compound which activates the receptor, usually by interaction with (binding) the ligand binding domain of the receptor. However, ligand can also include compounds which activate the receptor without binding.

"Agonist" is a compound which interacts with the steroid hormone receptor to promote a transcriptional response. Example estrogen is an agonist for the estrogen receptor, compounds which mimic estrogen would be defined as steroid hormone receptor agonists.

"Antagonist" is a compound which interacts with or binds to a steroid hormone receptor and blocks the activity of a receptor agonist.

The term "non-natural ligands" refer to compounds which are normally not found in animals or humans and which bind to the ligand binding domain of a receptor.

The term "anti-hormones" refers to compounds which are receptor antagonists. The anti-hormone is opposite in activity to a hormone.

The term "non-native ligands" refers to those ligands which are not naturally found in the specific organism (man or animal) in which gene therapy is contemplated. For example, certain insect hormones such as ecdysone are not found in humans. This is an example of a non-native hormone to the human or animal.

Examples of non-natural ligands, anti-hormones and non-native ligands include the following: 11β-(4-dimethylaminophenyl)-17β-hydroxy-17α-propinyl-4,9-estradiene-3-one (RU38486 or Mifepristone); 11β-(4-dimethylaminophenyl)-17α-hydroxy-17β-(3-hydroxypropyl)-13α-methyl-4,9-gonadiene-3-one (ZK98299 or Onapristone); 11β-(4-acetylphenyl)-17β-hydroxy-17α-(1-propinyl)-4,9-estradiene-3-one (ZK112993); 11β-(4-dimethylaminophenyl)-17β-hydroxy-17α-(3-hydroxy-1(Z)-propenyl-estra-4,9-diene-3-one (ZK98734); (7β,11β,17β)-11-(4-dimethylaminophenyl)-7-methyl-4',5'-dihydrospiro(ester-4,9-diene-17,2'(3'H)-furan)-3-one (Org31806); (11β,14β,17α)-4',5'-dihydro-11-(4-dimethylaminophenyl)-(spiroestra-4,9-diene-17,2'(3'H)-furan)-3-one (Org31376); 5-alpha-pregnane-3,20-dione.

The term "genetic material" as used herein refers to contiguous fragments of DNA or RNA. The genetic material which is introduced into targeted cells according to the methods described herein can be any DNA or RNA. For example, the nucleic acid can be: (1) normally found in the targeted cells, (2) normally found in targeted cells but not expressed at physiologically appropriate levels in targeted cells, (3) normally found in targeted cells but not expressed at optimal levels in certain pathological conditions, (4) novel fragments of genes normally expressed or not expressed in targeted cells, (5) synthetic modifications of genes expressed or not expressed within targeted cells, (6) any other DNA which may be modified for expression in targeted cells and (7) any combination of the above.

The term "nucleic acid cassette" as used herein refers to the genetic material of interest which can express a protein, or a peptide, or RNA after it is incorporated transiently, permanently or episomally into a cell. The nucleic acid cassette is positionally and sequentially oriented in a vector with other necessary elements such that the nucleic acid in the cassette can be transcribed and, when necessary, translated in the cells.

"Mutant" refers to an alteration of the primary sequence of a receptor such that it differs from the wild type or naturally occurring sequence. The mutant steroid hormone receptor protein as used in the present invention can be a mutant of any member of the steroid hormone receptor superfamily. For example, a steroid receptor can be mutated by deletion of amino acids on the carboxy terminal end of the protein. Generally, a deletion of from about 1 to about 120 amino acids from the carboxy terminal end of the protein provides a mutant useful in the present invention. A person having ordinary skill in this art will recognize, however, that a shorter deletion of carboxy terminal amino acids will be necessary to create useful mutants of certain steroid hormone receptor proteins. For example, a mutant of the progesterone receptor protein will contain a carboxy terminal amino acid deletion of from about 1 to about 60 amino acids. In a preferred embodiment 42 carboxy terminal amino acids are deleted from the progesterone receptor protein.

"Null mutation" is a genetic lesion to a gene locus that totally inactivates the gene product.

The term "plasmid" as used herein refers to a construction comprised of extrachromosomal genetic material, usually of a circular duplex of DNA which can replicate independently of chromosomal DNA. Plasmids are used in gene transfer as vectors. Plasmids which are helpful in the present invention include plasmids selected from the group consisting of UP-1, YEphPR-A879, YEphPR-A891, YEphPR-B891, YEphPR-B879, phPR-A879, phPR-A891, phPR-B879 and phPR-B891.

The term "vector" as used herein refers to a construction comprised of genetic material designed to direct transformation of a targeted cell. A vector contains multiple genetic elements positionally and sequentially oriented with other necessary elements such that the nucleic acid in a nucleic acid cassette can be transcribed and when necessary translated in the transfected cells. In the present invention the preferred vector comprises the following elements linked sequentially at appropriate distance for allowing functional expression: a promoter; a 5' mRNA leader sequence; an initiation site; a nucleic acid cassette containing the sequence to be expressed; a 3' untranslated region; and a polyadenylation signal.

As used herein the term "expression vector" refers to a DNA plasmid that contains all of the information necessary to produce a recombinant protein in a heterologous cell.

The term "vehicle" as used herein refers to non-genetic material combined with the vector in a solution or suspension which enhances the uptake, stability and expression of genetic material into targeted cells. Examples of a vehicle include: sucrose, protamine, polybrene, spermidine, polylysine, other polycations, proteins, $CaPO_4$ precipitates, soluble and insoluble particles, or matrices for slow release of genetic material. The proteins may be selected from the group including lactoferrin, histone, natural or synthetic DNA binding proteins, natural or synthetic DNA binding compounds, viral proteins, non-viral proteins or any combinations of these. In addition, vehicles may be comprised of synthetic compounds which bind both to DNA and function as ligands for normal receptors on targeted cells.

The term "transformed" as used herein refers to transient, stable or persistent changes in the characteristics (expressed phenotype) of a cell by the mechanism of gene transfer. Genetic material is introduced into a cell in a form where it expresses a specific gene product or alters the expression or effect of endogenous gene products. One skilled in the art readily recognizes that the nucleic acid cassette can be introduced into the cells by a variety of procedures, including transfection and transduction.

The term "transfection" as used herein refers to the process of introducing a DNA expression vector into a cell. Various methods of transfection are possible including microinjection, $CaPO_4$ precipitation, liposome fusion (e.g. lipofection) or use of a gene gun.

The term "transduction" as used herein refers to the process of introducing recombinant virus into a cell by infecting the cell with a virus particle. In the present invention, the recombinant virus contains a nucleic acid cassette.

The term "transient" as used herein relates to the introduction of genetic material into a cell to express specific proteins, peptides, or RNA, etc. The introduced genetic material is not integrated into the host cell genome or replicated and is accordingly eliminated from the cell over a period of time.

The term "stable" as used herein refers to the introduction of genetic material into the chromosome of the targeted cell where it integrates and becomes a permanent component of the genetic material in that cell. Gene expression after stable transduction can permanently alter the characteristics of the cell leading to stable transformation.

The term "persistent" as used herein refers to the introduction of genes into the cell together with genetic elements which enable episomal (extrachromosomal) replication. This can lead to apparently stable transformation of the characteristics of the cell without the integration of the novel genetic material into the chromosome of the host cell.

The term "pharmacological dose" as used herein with a vector/molecular switch complex refers to a dose of vector and level of gene expression resulting from the action of the promoter on the nucleic acid cassette when introduced into the appropriate cell type which will produce sufficient protein, polypeptide, or antisense RNA to either (1) increase the level of protein production, (2) decrease or stop the production of a protein, (3) inhibit the action of a protein, (4) inhibit proliferation or accumulation of specific cell types, or (5) induce proliferation or accumulation of specific cell types. The dose will depend on the protein being expressed, the promoter, uptake and action of the protein RNA. Given any set of parameters, one skilled in the art will be able to determine the dose.

The term "pharmacological dose" as used herein with a ligand refers to a dose of ligand sufficient to cause either up-regulation or down-regulation of the nucleic acid cassette. Thus, there will be a sufficient level of ligand such that it will bind with the receptor in the appropriate cells in order to regulate the nucleic acid cassette. The specific dose of any ligand will depend on the characteristics of the ligand entering the cell, binding to the receptor and then binding to the DNA and the amount of protein being expressed and the amount of up-regulation or down-regulation needed. Given any set of parameters, one skilled in the art will be able to determine the appropriate dose for any given receptor being used as a molecular switch.

"Plasmid activity" is a phenotypic consequence that relates specifically to introduction of a plasmid into an assay system.

"Transcriptional activity" is a relative measure of the degree of RNA polymerase activity at a particular promotor.

"Receptor activity" is a phenotypic consequence that relates specifically to introduction of a receptor into an assay system.

The present invention provides mutant steroid hormone receptor proteins. These mutated steroid hormone receptor proteins are capable of distinguishing, and are useful in methods of distinguishing a steroid hormone receptor antagonist from a steroid hormone receptor agonist.

The present invention further provides plasmids containing mutated steroid hormone receptor proteins. Plasmids of the present invention may contain mutant proteins of any of the hormones in the steroid hormone receptor superfamily.

The present invention also provides transfected cells containing plasmids having mutated steroid hormone receptor proteins inserted therein. Useful cells for transfection include yeast, mammalian and insect cells.

In a specific embodiment, the yeast is *Saccharomyces cerevisiae*. In a specific embodiment the mammalian cell is selected from the group consisting of HeLa, CV-1, COSM6, HepG2, CHO and Ros 17.2. In a specific embodiment the insect cells are usually selected from the group consisting of SF9, drosophilia, butterfly and bee.

The present invention also provides stable cell lines transformed with the plasmids of the present invention.

The plasmids and transfected cells of the present invention are useful in methods of determining whether a compound has antagonist or agonist activity at a steroid hormone receptor. This method comprises contacting a compound of interest with a transfected cell of the present invention. If the compound induces transcription, it has a steroid hormone receptor antagonist. If no transcription is induced, the compound may be a steroid hormone receptor agonist.

The present invention also provides a method of determining an endogenous ligand for a steroid hormone receptor protein. This method comprises initially contacting a compound with a transfected cell of the present invention. Subsequently, the transcription level induced by the compound is measured. The higher the transcription level the more strongly the indication that the compound is an endogenous ligand of the specific receptor being tested.

In addition, the present invention provides endogenous ligands for steroid hormone receptor proteins. An endogenous ligand for a steroid hormone receptor protein is capable of stimulating transcription when in the presence of a transfected cell of the present invention. The endogenous ligand binds to the mutated steroid receptor of the present invention and stimulates transcription in cells containing the mutated receptor.

Another alternative embodiment of the present invention is a molecular switch for regulating expression of a heterologous nucleic acid sequence in gene therapy.

In a preferred embodiment of the present invention, the molecular switch for regulating expression of a heterologous nucleic acid cassette in gene therapy, comprises a modified steroid receptor which includes a natural steroid receptor DNA binding domain attached to a modified ligand binding domain. In the preferred embodiment of the molecular switch the modified binding domain usually binds only ligand compounds which are non-natural ligands, anti-hormones or non-native ligands. One skilled in the art readily recognizes that the modified ligand binding domain may bind native ligands, but there is insignificant binding and thus very little, if any, regulation.

In a preferred embodiment, the modified steroid receptor is a progesterone receptor with the DNA binding domain replaced with a DNA binding domain selected from the group consisting of GAL-4 DNA, virus DNA binding site, insect DNA binding site and a non-mammalian DNA binding site.

The molecular switch can be further modified by the addition of a transactivation domain. The transactivation domains which are usually used include VP-16, TAF-1, TAF-2, TAU-1 and TAU-2. One skilled in the art will readily recognize that a variety of other transactivation domains are available.

In a preferred embodiment the progesterone receptor has the modified ligand binding domain GAL-4 DNA binding domain and a transactivation domain such as TAF-1.

In a further embodiment, the progesterone receptor has the ligand binding domain replaced with an ecdysone binding domain. Again, the function of this molecular switch can be enhanced by adding a TAF-1 transactivation domain.

One skilled in the art will readily recognize the molecular switch can be made tissue specific by selecting the appropriate transactivation domains, ligand binding domains and DNA binding domains. In particular, one skilled in the art readily recognizes that by adding a transactivation domain which is specific to a given tissue, the molecular switch will only work in that tissue. Also, the addition of a tissue-specific cis-element to the target gene will aid in providing tissue-specific expression.

The present invention also envisions a method of regulating gene expression of a nucleic acid cassette in gene therapy. This method comprises the step of attaching the molecular switch to a nucleic acid cassette used in gene therapy. In the preferred embodiment, the nucleic acid sequence which is expressed is heterologous. The combined nucleic acid cassette/molecular switch is then administered in a pharmacological dose to an animal or human to be treated or to a transgenic animal or to a plant.

One skilled in the art readily appreciates that the combined nucleic acid cassette/molecular switch can be introduced into the cell in a variety of ways both in vivo and ex vivo. The introduction can be by transfection or transduction. After the nucleic acid cassette/molecular switch is introduced into the cell, the cassette in the resultant transformed cell can be either up-regulated (turned on) or down-regulated (turned off) by introducing to the animal or human a pharmacological dose of a ligand which binds the modified ligand binding site.

In one embodiment of the present invention there is a method for regulating nucleic acid cassette expression in gene therapy comprising the step of linking a molecular switch to a nucleic acid cassette. This molecular switch/nucleic acid cassette is introduced into a cell to form a transformed cell. The transformed cell is then inserted in a pharmacological dose into a human or animal for gene therapy.

In another embodiment the molecular switch/nucleic acid cassette is directly injected into a targeted cell in vivo for gene therapy.

For example, in the treatment of senile dementia or Parkinson's disease, the nucleic acid cassette within the nucleic acid cassette contains a growth factor, hormone or neurotransmitter and the cell is a brain cell. In a preferred embodiment the naked brain cell containing the cassette can be encapsulated in a permeable structure. The naked brain cell or the permeable structure containing the brain cell is then inserted into the animal or human to be treated. The permeable structure is capable of allowing the in/out passage of activators of the molecular switch and growth factors but prevents the passage of attack cells that would interact with and damage the implanted brain cells. In the preferred embodiment it is important to encapsulate the brain cells, since introduction of naked brain cells often results in attack by the body's defense system and the destruction of these cells. One skilled in the art recognizes that a variety of encapsulation procedures and structures are available in the art.

In the treatment of senile dementia or Parkinson's disease, it is found that the molecular switch in the preferred embodiment includes a progesterone receptor with the modified ligand binding domain replaced attached to a GAL-4 DNA. A growth factor is produced in the transformed cell by giving a pharmacological dose of an appropriate ligand to turn the molecular switch on (up-regulation) to the animal or human to be treated. For example, an anti-progesterone such as RU38486 can be given. The amount of growth factor produced is proportional to the dose of ligand given. One skilled in the art will be able to determine a pharmacological dose depending on the molecular switch used and the ligand used.

Another embodiment of the present invention employs a dual system of agonist/antagonist pairs. In this system a custom up-regulation ligand is chosen and the desired receptor mutation or modified receptors are made. Then a second round of ligand screening and mutation is performed to develop a receptor which also binds a specific, selective down-regulator ligand. In the preferred embodiment the ligands share a normal metabolic clearance pathway of the host's endogenous ligands, thereby avoiding problems of toxicity and long half-life. In the screening process either yeast, animal or insect cells can be used. In the preferred embodiment yeast cells are used.

In addition to selecting transactivation elements and receptors for tissue specificity, one skilled in the art also recognizes that tissue specificity can be achieved with specific ligands. For example, ligands can be chosen which act only in certain tissues due to requirements for terminal conversion to active metabolites. A synthetic androgen which binds a transfected androgen receptor is made. This androgen, however, requires metabolism to the 5-alpha reduced form to be active. In this manner only classical androgen end-organs are able to metabolize the new ligand to its proper chemical form. Other cells of the body lacking the 5-alpha reductase will not activate the transgene via this compound.

Alternatively, a ligand which is active only when it is not further metabolized to the 5-alpha reduced form is used. In this case, the ligand would be active only in classical androgen end-organ cells. Since 5-alpha reductase inhibitors are currently available therapeutic agents, they can be used in conjunction with the present invention to allow complete shutdown or complete activation of the receptor bypassing the ligand route if some sort of emergency required that approach.

Side chains are usually tolerated at certain positions on ligands of the receptor superfamily. For example, the 7-alpha position of certain ligands, such as estradiol and progesterone, can be attached to sidechains and the ligands will still bind to receptors. Suitable sidechains can be used to either increase or restrict solubility, membrane transfer or target organ accessibility. Thus, even specific ligands can be made to show tissue preference. For example, the synthetic steroid R5020 (17α,21-dimethyl-19-Norpregna-4,9-diene-3, 20-dione) does not enter tissue culture cells at low temperatures at which progesterone enters freely. One skilled in the art readily recognizes that other modifications can be made to ligands to tailor their use as up- or down-regulating agents in the present invention.

The following samples are offered by way of illustration and are not intended to limit the invention in any way.

EXAMPLE 1

The homogenization buffer for hormone binding assays contained 10 mM Tris-HCl, 1.5 mM EDTA, 1 mM dithiothreitol, pH 7.4 (TESH buffer). The homogenization buffer for Western analysis of receptor contained 10 mM Tris-HCl, 2 mM EDTA, 45 mM dithiothreitol, 10% glycerol and 300 mM NaCl (TEDG+salts).

Yeast Strain

The *Saccharomyces cereuisiae* strain BJ3505 (MATα, pep4:HIS3, prb1-Δ1.6R, his3Δ200, lys2-801, trp1-Δ101, ura3-52, gal2, (CUP1)) was used (Yeast Genetic Stock Center, Berkeley, Calif.). All yeast transformations were carried out following the lithium acetate transformation protocol (Ito, et al., *J. Bacteriol.* 153:163–168, 1983).

The PCR reactions were carried out using YEphPR-B DNA template (a YEp52AGSA-derived yeast expression plasmid containing the cDNA of hPR form-B (Misrahi, et al., *Biochem. Bioph. Res. Comm.* 143:740–48, 1987) inserted downstream of the yeast methallothionein-CUP1 promoter) and using three different sets of primers. In order to decrease the fidelity of the second strand polymerization reaction, buffer conditions of 1.5 mM $MgCl_2$, 0.1 mM dNTPs and pH 8.2 were used. About 2000 primary transformants were obtained from each region-specific library.

EXAMPLE 2

Yeast Mutant Screening

Colonies of each library of hPR molecules mutated in specific subregions were pooled, large amounts of DNA were prepared and used to transform yeast cells carrying the reporter plasmid YRpPC3GS+, which contains two GRE/PRE elements upstream of the CYC1 promoter linked to the Lac-Z gene of *E. coli* (Mak, et al., *J. Biol. Chem.* 265:20085–20086, 1989). The transformed cells were plated on 1.5% agar plates containing 2% glucose, 0.5% casamino acids (5% stock solution of casamino acids is always autoclaved before use to destroy tryptophan), 6.7 g/l yeast nitrogen base (without amino acids) and 100 µM CuSO4 (CAA/Cu plates) and grown for 2 days at 30° C. These colonies were then replica-plated on CAA/Cu plates containing 0.16 g/l of 5-bromo-4-chloro-3-indolyl-β-D-galactoside (X-Gal, an indicator of β-galactosidase activity) with or without the hormones as indicated in FIG. 1 and allowed to grow for one day at 30° C., then two days at room temperature in the dark.

EXAMPLE 3

Growth of Yeast Culture for in vitro Assay

*Saccharomyces cerevisiae* cells containing YEphPRB and the reporter plasmid were grown overnight at 30° C. in minimal media containing 2% glucose. The cells were subcultured in fresh medium and allowed to grow until early mid-log phase ($O.D._{600nm}=1.0$). Induction of receptor was initiated by the addition of 100 µM copper sulfate to the culture. Cells were harvested by centrifugation at 1,500×g for 10 minutes and resuspended in the appropriate buffer. This and all subsequent steps of analysis of the yeast extracts were done at 4° C.

EXAMPLE 4

Transcription Assay

Yeast cells containing the reporter and expression plasmids were grown overnight as described above in Example 3 in the presence of 100 µM copper sulfate. When the cell density reached $O.D._{600nm}=1.0$, hormones were added to the cultures. After a 4 hour incubation, yeast extracts were prepared and assayed for β-galactosidase activity as described previously (Miller, J. M. Miller ed., 352–355, 1972).

Generally, reporters useful in the present invention are any which allow for appropriate measurement of transcription levels. Preferable reporter systems include reporter vectors comprised of the yeast iso-1-cytochrome C proximal promoter element fused to a structural gene, wherein said structural gene is selected from the group consisting of β-galactosidase, galactokinase and URA3. More preferably, the vector is comprised of an insertion site for a receptor response element. The vectors which include β-galactokinase as an indicator of transcriptional activity are derived from the parent vector PC2 while the vectors which include galactokinase are derived from YCpR1 vector. Preferably, the structural genes originate from *E. coli*.

EXAMPLE 5
Western Immunoblotting

Yeast cells were grown as described in Example 4 for the transcription assay. Yeast extracts for Western blot analysis were prepared by resuspending the cell pellet in TEDG+ salts. The cell suspension was mixed with an equal volume of glass beads and disrupted by vortexing in a microcentrifuge tube. The homogenate was centrifuged at 12,000×g for 10 minutes. The supernatant was collected and the protein concentration was estimated using bovine serum albumin as standard. Yeast extracts were resolved on a 0.1% sodium dodecyl sulfate-7% polyacrylamide gel and transferred to Immobilon membrane as described previously (McDonnell, et al., *Mol. Cell. Biol.* 9:3517–3523, 1989). Solid phase radioimmunoassay was performed using a monoclonal antibody (JZB39) directed against the N-terminal domain of A and B forms of hPR.

EXAMPLE 6
Hormone Binding Competition Assays

Induction of PR synthesis was initiated by the addition of 100 μM $CuSO_4$ to the culture and incubation was continued for 6 hours. The cell pellet was resuspended in TESH buffer containing 1 μg/ml leupeptin, 10 μg/ml PMSF and 10 μg/ml pepstatin. The cell suspension was mixed with an equal volume of glass beads (0.5 mm; B. Braun Instruments) and disrupted by vortexing in a microcentrifuge tube. The homogenate was centrifuged at 12,000×g for 10 minutes and the supernatant was further centrifuged at 100,000×g for 30 minutes to obtain a cytosol fraction. Diluted yeast extracts (200 μl) containing 100 μg of total protein were incubated overnight at 4° C. with [$^3$H]ligand in the absence (total binding) or presence (non-specific binding) of a 100-fold excess of unlabelled ligand. Bound and free steroids were separated by addition of 500 μl of dextran-coated charcoal suspension (0.5% Norit A, 0.05% dextran, 10 mM Tris HCl, pH 7.4 and 1 mM EDTA). Specific binding was determined by subtracting nonspecific from total binding. Scatchard analysis was carried out as described previously by Mak, et al., *J. Biol. Chem.* 264:21613:21618 (1989).

EXAMPLE 7
Site-directed Mutagenesis

Mutants YEphPR-B879 and YEphPR-B891 were prepared following the procedure described by Dobson, et al., *J. Biol. Chem.* A264:4207–4211 (1989). CJ236 cells were infected with mpPR90 (an M13 plasmid containing hPR cDNA). The resulting uridine-containing single-stranded DNA was annealed to 20-mer oligonucleotides containing a TGA stop codon corresponding to amino acids 880 and 892, respectively.

EXAMPLE 8
Construction of Mammalian Expression Vectors

The mammalian expression vector phPR-B contains the SV40 enhancer sequence upstream of the human growth hormone promoter linked to the hPR-B cDNA. This vector was digested with Sal1 and EcoR1. The 6.1 kb fragment (containing the vector sequences and the 5'-1.5 kb of the hPR) was gel-purified and ligated to the 2.1 kb fragment of YEphPR-B891 (containing the 3'-end of the receptor). previously cut with Sal1 and EcoR1. The resulting plasmid, phPR-B891, encodes a 42 amino acid truncated version of hPR form B.

EXAMPLE 9
Mammalian Cell Transient Transfections and CAT-Assays

Five μg of chloramphenicol acetyltransferase (CAT) reporter plasmid, containing two copies of a PRE/GRE from the tyrosine amino transferase gene linked to the thymidine kinase promoter (PRETKCAT), were used in transient cotransfection experiments together with 5 μg of wild type or mutant receptor DNAs. Transient cotransfections and CAT-assays were performed as described by Tsai, et al., *Cell* 57:443–448 (1989).

EXAMPLE 10
Mutagenesis of the Hormone Binding Domain of hPR-B

In order to characterize amino acids within the hPR HBD which are critical for ligand binding and hormone-dependent transactivation, libraries of mutated hPR molecules were created and the mutants introduced into a reconstituted progesterone-responsive transcription system in yeast. This system allowed the screening of large numbers of mutant clones and the direct, visual identification of phenotypes.

Unique restriction sites for NaeI, AvrII and EcoNI were created in the cDNA of hPR, obtaining three cassettes of 396, 209 and 400 nucleotides (regions 1, 2 and 3, respectively). For PCR mutagenesis three sets of primers (16+7 for region 1, 5+4 for region 2 and 6+13 for region 3) were used in the polymerization reaction using YEphPR-B as DNA template. The fragments obtained after PCR were digested with the appropriate enzymes, gel-purified and ligated into the parental plasmid YEphPR-B. Ligation mixes were used to transform bacterial cells and to obtain libraries of hPR molecules randomly point-mutated in the HBD. 5 μg of DNA were used from each library to transform yeast cells carrying the reporter plasmid YRpPC3GS+ and transformants were selected for tryptophan and uracil auxotrophy on CAA plates containing 100 μM $CuSO_4$. These were then replicated on CAA plates containing the hormones. The screening for "up-mutations" allowed identification of receptor mutants with hormone-independent transcriptional activity, or increased affinity for the ligand (these clones should remain blue when grown with 100-fold less hormone), or with an altered response to RU38486 or a glucocorticoid analogue. In the "down-mutation" screening, receptor mutants that were transcriptionally inactive in the presence of the ligand were detected.

Because of the nature of the method used to generate the mutated DNA templates, it was necessary, firstly, to determine the quality of the libraries obtained. This was assessed by estimating the number of null-mutations generated by mutagenesis. We estimated the frequency of occurrence of transcriptionally inactive receptors (white colonies) compared to the total number of colonies. This frequency was about 7%.

The primary transformants were replica-plated onto plates containing the antiprogestin RU38486. The wild type receptor is not activated by this hormone (FIG. 1). Using this screening strategy, a single colony was identified that displayed considerable transcriptional activity in response to the antihormone. Interestingly, the same colony did not display transcriptional activity when replica-plated in the presence of progesterone. The colony was purified and the phenotype was confirmed. Eviction of the expression vector from the clone, followed by reintroduction of the unmutated receptor, demonstrated that the phenotype was indeed related to the expression vector and was not the result of a secondary mutation. In addition, the mutated plasmid called UP-1, was rescued from yeast by passage through *E.coli* (as described in Ward, *Nucl. Acids Res.* 18:5319 (1990) and purified. This DNA was then reintroduced into yeast that contained only the reporter plasmid. As expected, the mutant phenotype was stable and related directly to the receptor expression plasmid.

EXAMPLE 11
Characterization of the UP-1 Mutant

The plate assays used to identify the receptor mutants are qualitative in nature. To further characterize the properties of UP-1, the activity of the receptor mutants was compared with that of the wild type receptor in a transcription assay. In this method, yeast cells transformed with either the wild type or the mutant receptor and a progesterone responsive reporter were grown overnight in the presence of 100 $\mu$M $CuSO_4$. When the cells had reached an $O.D._{600nm}$ of 1.0, they were supplemented with progesterone or RU38486 and harvested by centrifugation after four hours. The β-galactosidase activity in the cell cytosol was then measured.

Figure 2A:
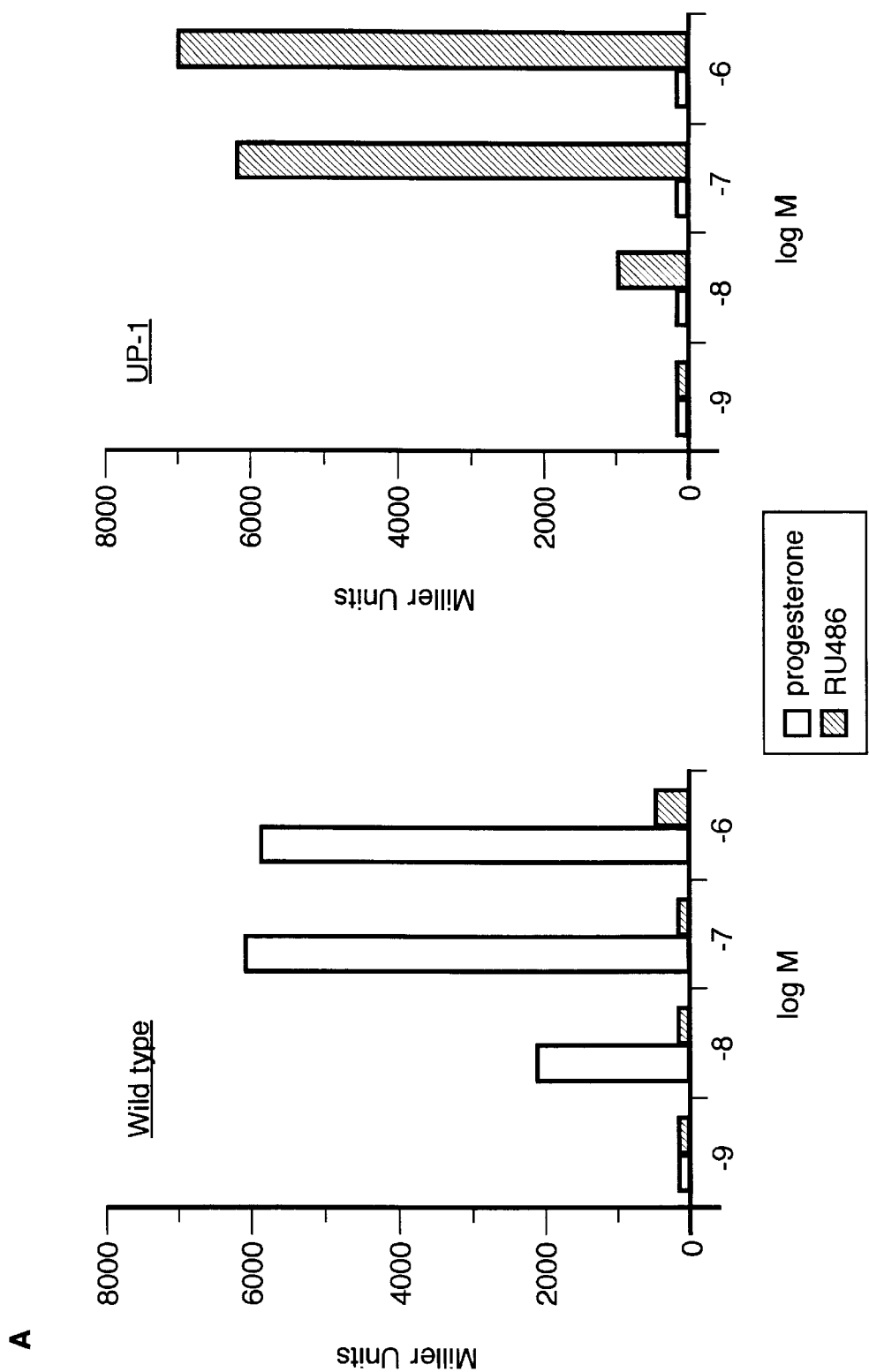
FIGS. 2A & B illustrates the functional and structural characterization of the UP-1 mutant.

With reference to FIG. 2, panel (A), when assayed with the wild type receptor, 1 $\mu$M RU38486 is a weak inducer of transcription, whereas progesterone caused a greater than 60-fold induction of transcription at 1 $\mu$M. However, this situation was reversed when the mutant was analyzed. In this case, RU38486 was an extremely potent activator, whereas progesterone was ineffective. Interestingly, the activity achieved by the mutant in the presence of RU38486 was of the same order of magnitude as that of the wild type assayed in the presence of progesterone. This reversal in specificity clearly indicates that the mechanism by which these ligands interact with the receptor is basically different.

FIG. 2 shows the DNA and amino acid sequences of the wild type and mutant DNAs. The cytosine at position 2636 was missing in the mutant DNA, therefore, a shifted reading frame was created and a stop codon was generated 36 nucleotides downstream of the C-2636 deletion. A schematic structure of the wild type and UP-1 receptors is also presented with a depiction of the 12 C-terminal amino acids unique to the mutant receptor. Conserved and structurally similar amino acids are marked by an apostrophe and asterisk, respectively.

Figure 2B:
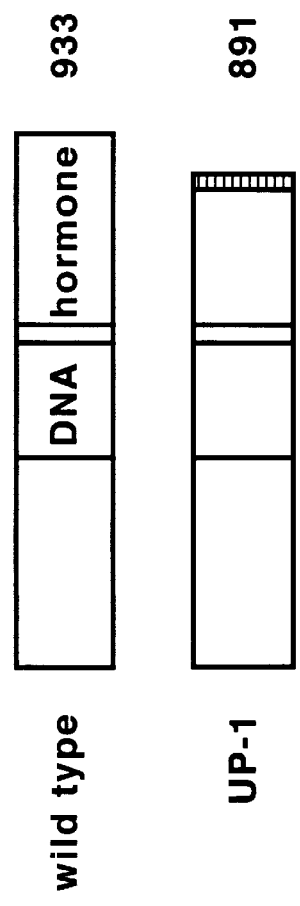

DNA sequence analysis of UP-1 identified a single nucleotide deletion at base 2636 (FIG. 2B). This mutation results in a shift of the reading frame which generates a stop codon 36 nucleotides downstream. As a result, the wild type receptor is truncated by 54 authentic amino acids and 12 novel amino acids are added at the C-terminus.

EXAMPLE 12
Western Analysis of the Mutant Human Progesterone Receptor

Figure 3:
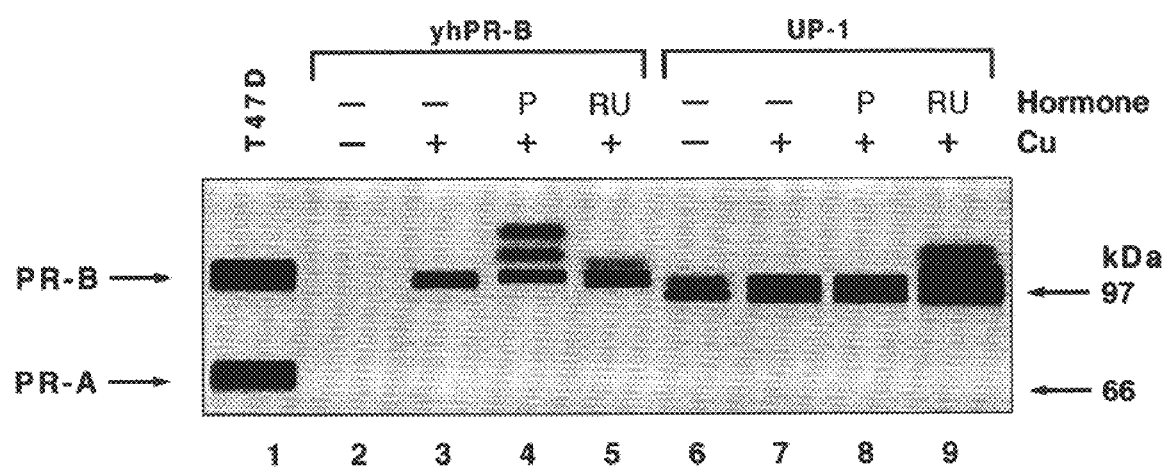
FIG. 3 shows a western analysis of the mutant human progesterone receptor.

FIG. 3 shows a western analysis of mutant hPR. Yeast cells carrying the reporter plasmid and wild type (yhPR-B__ or mutant (UP-1) hPR were grown overnight in CAA medium with (lanes 3 to 5 and 7 to 9) or without (lanes 2 and 6) 100 $\mu$M $CuSO_4$. 1 $\mu$M progesterone or 1 $\mu$M RU38486 were added as indicated and cells were grown for another 4 hours. Yeast extracts were prepared as described above. 50 $\mu$g of protein extract were run on a 0.1% SDS-7% polyacrylamide gel. 50 $\mu$g of a T47D nuclear extract containing the A and B forms of hPR were also loaded (lane 1) as a positive control. The positions of molecular weight markers are indicated.

A Western immunoblot analysis of UP-1 and wild type receptors was performed in order to verify that the mutant receptor was synthesized as predicted from its DNA sequence and to eliminate the possibility that some major degradation products were responsible for the mutant phenotype. As shown in FIG. 3, the mutant receptor migrated faster in the gel, confirming the molecular weight predicted by DNA sequencing. The wild type receptor (yhPR-B) ran as a 114 kDa protein, while the mutant receptor was 5 kDa smaller (compare lanes 2 and 3 with 6 and 7). The addition of 100 $\mu$M $CuSO_4$ to the cell cultures increased synthesis of both the wild type and mutant hPR to the same extent. No major degradation products were detected. In the presence of progesterone and RU38486, yhPR-B bands were upshifted due to hormone-induced phosphorylation of the receptor. In contrast, RU38486 induced upshifting of wild type PR to a lesser extent (lanes 4 and 5). For the UP-1 mutant this hormone-dependent upshifting was seen upon treatment with RU38486 (lanes 8 and 9). Thus, the C-terminus of PR may be responsible for the inactivity of RU38486. Consequently, removal of this sequence would enable RU38486 to become an agonist.

EXAMPLE 13
Hormone Binding Analysis

FIG. 4 shows the transcriptional activity and hormone binding analysis of wild type and mutant hPR constructs. hPR constructs are reported to the left side together with a schematic representation of the receptor molecules. Yeast cells were grown in the presence of 100 $\mu$M $CuSO_4$. Transcriptional analysis was done as described above. Experiments were done in triplicate and transcriptional activities were normalized with respect to protein. Hormone binding assays were performed in the presence of 20 nM [$^3$H] progesterone or 20 nM [$^3$H] RU38486.

A saturation binding analysis of the UP-1 mutant receptor was performed in order to determine if its affinity for RU38486 and progesterone was altered. Scatchard analysis of the binding data demonstrated that both the wild type and mutant receptors had a similar affinity for RU38486 of 4 and 3 nM, respectively. As seen in FIG. 4, the mutant receptor molecule had lost the ability to bind progesterone. Thus, the amino acid contacts for progesterone and RU38486 with hPR are different.

Generation of Deletion Mutants of hPR-B

As shown in FIG. 2B, DNA sequencing revealed that the frameshift mutation in the UP-1 clone created a double mutation in the receptor protein. That is, a modified C-terminal amino acid sequence and a 42 amino acid truncation. In order to identify which mutation was ultimately responsible for the observed phenotype, two new receptor mutants were constructed in vitro: YEphPR-B879, containing a stop codon corresponding to amino acid 880, and YEphPR-B891, containing a stop codon at amino acid 892. Hormone binding data (see FIG. 4) demonstrated that both of these truncated receptors could bind RU38486 but not progesterone. When examined in vivo, both mutant receptors activated transcription in the presence of RU38486 to levels comparable to those of the mutant UP-1 generated in yeast. As expected, both mutants were inactive in the presence of progesterone. Thus, the observed phenotype was not due to second site mutations in the UP-1 molecule. Also, 12 additional amino acids, from 880 to 891, were not responsible for the mutant activity. In addition, it is clear the C-terminal 42 amino acids are required for progesterone to bind to the receptor while the last 54 amino acids are unnecessary for RU38486 binding. Thus, the antagonist is contacting different amino acids in the native receptor molecule and may induce a distinct receptor conformation relative to agonists.

EXAMPLE 14
Steroid Specificity for Activation of Transcription of the UP-1 Mutant FIG. 5 shows the specificity of the transcriptional activity of the mutant hPR. In panel (A), wild type and UP-1 mutant receptor transcriptional activities were assayed in the presence of different concentrations of progesterone, RU38486, Org31806 and Org31376 as indicated.

Figure 5A:
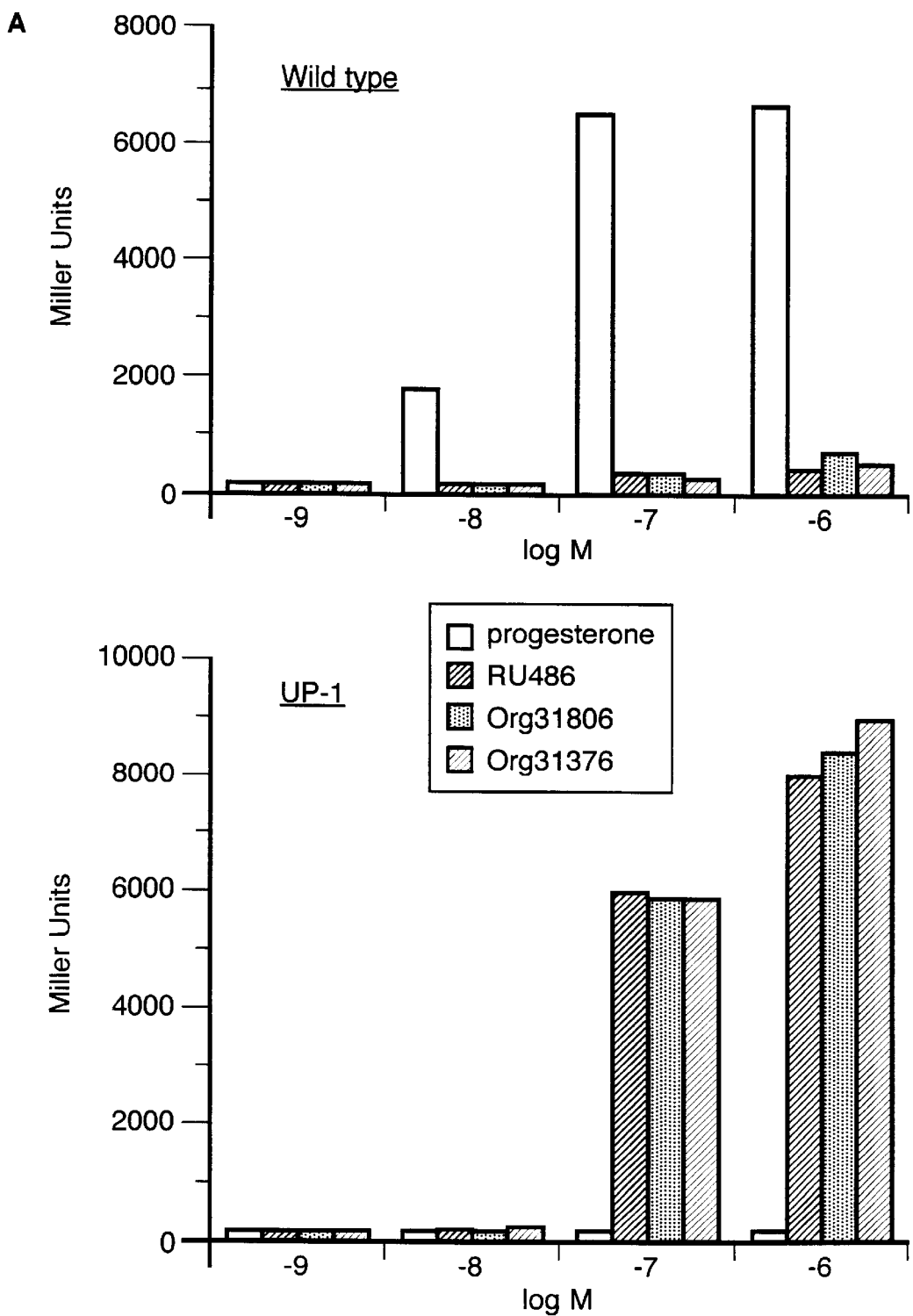
FIGS. 5A & B shows the specificity of transcriptional activity of the mutant human progesterone receptor.

A transcription assay was performed using two synthetic antagonists, Org31806 and Org31376, which are potent antiprogestins. As shown in FIG. 5A, the mutant receptor was activated by both of these compounds. The curve of the concentration-dependent activity was similar to that obtained with RU38486, suggesting that the affinity of these two antagonists for the mutant receptor is similar to that of RU38486. When assayed with the wild type receptor, these compounds had minimal transcriptional activity and behaved like partial agonists (3–10% of progesterone activity) only at concentrations of 1 μM, as does RU38486. Thus, the inhibitory effect of the C-terminus of hPR extends to other receptor antagonists.

Figure 5B:
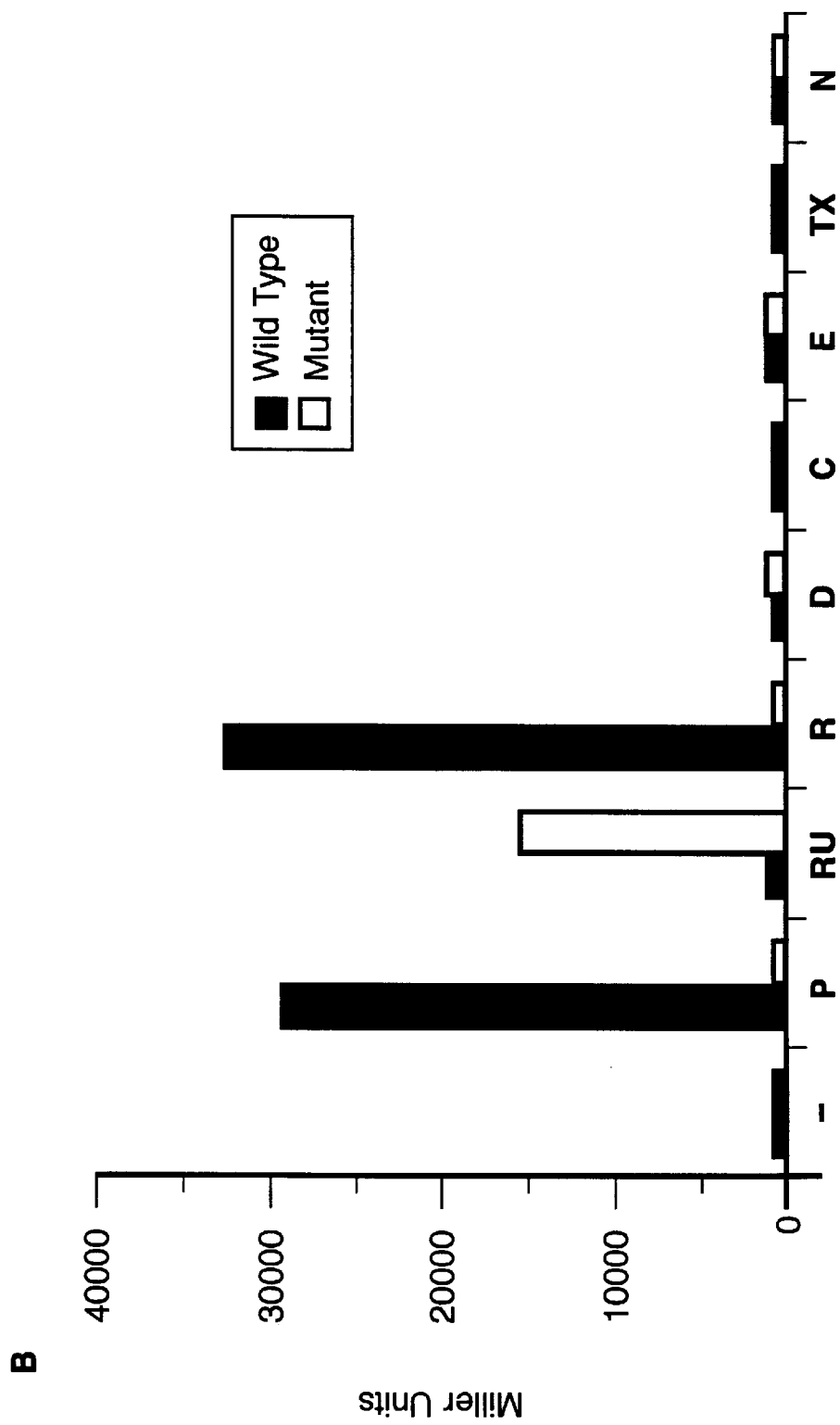

In panel (B), transcriptional activities of wild type and UP-1 mutant receptors were assayed in the presence of 1 μM progesterone (P), RU38486 (RU), R5020 (R), dexamethasone (D), cortisol (C), estradiol (E), tamoxifen (TX) or nafoxidine (N) (see FIG. 5B). The synthetic agonist R5020 had no effect on the UP-1 mutant, suggesting that agonists, such as progesterone and R5020, require the C-terminus of the native receptor for binding and consequently fail to recognize the truncated UP-1 receptor. Other steroids known to enter yeast cells, such as estradiol, the antiestrogens tamoxifen and nafoxidine, dexamethasone and cortisol, might possibly activate the mutated receptor. All steroids tested were found to be inactive with either the wild type or mutant receptor. Thus, the activation of the mutant receptor is specific to antiprogestins.

EXAMPLE 15
Transcriptional Activity of Mutant Receptors in Mammalian Cells

FIG. 6 shows the transient transfection of mutant hPR into mammalian cells. In panel (A), HeLa cells were transiently transfected with phPR-B and pHPR-B891 receptors together with PRETKCAT receptor plasmid using the polybrene method of transfection as described (Tsai, et al. 1989). Cells were grown with or without 100 nM progesterone or RU38486 for 48 hours prior to harvesting. CAT assays were performed as described above. In panel (B), CV-1 cells were transiently transfected as in (A).

With reference to FIG. 6, mutant receptor activity was assayed in both human endometrial HeLa cells and monkey kidney CV-1 fibroblasts. A mutant, phPR-891, was constructed by replacing the full-length PR insert of phPR-B vector with the truncated PR cDNA of YEphPR-B891. The resulting receptor mutant, phPR-B891, is a 42 amino acid truncation of hPR-B form. Mutant 891 and wild type receptors were transfected into HeLa cells together with the PRETKCAT reporter plasmid, which contains two copies of a GRE/PRE element.

Figure 6A:
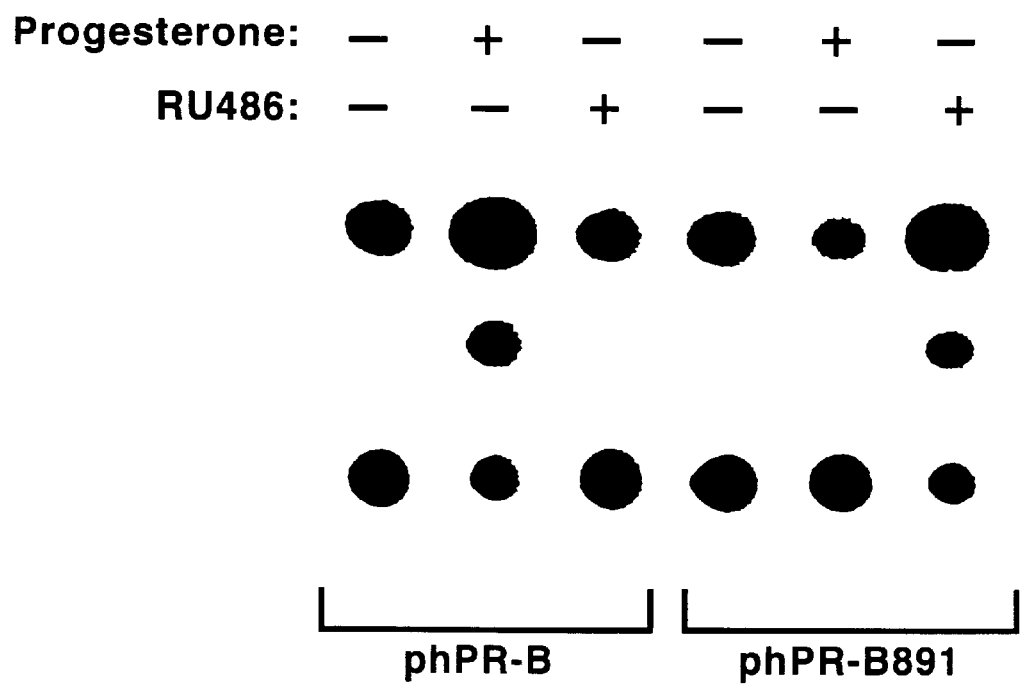
FIGS. 6A & B depicts the transient transfection of mutant human progesterone human receptor into mammalian cells.

As expected, wild type PR activated transcription of the CAT gene reporter in the presence of $10^{-7}$ M progesterone (FIG. 6A). Although basal transcription level was high, a 3- to 4-fold induction of transcription was detected when progesterone was added to the media. In contrast, no induction occurred in the presence of RU38486. The high basal level of transcription detected in these experiments may mask or alter an RU38486 effect on wild type hPR.

On the other hand, an induction of CAT activity was observed when the 891 mutant was incubated in the presence of $10^{-7}$ M RU38486 (FIG. 6A). The same concentration of progesterone had no activity.

Figure 6B:
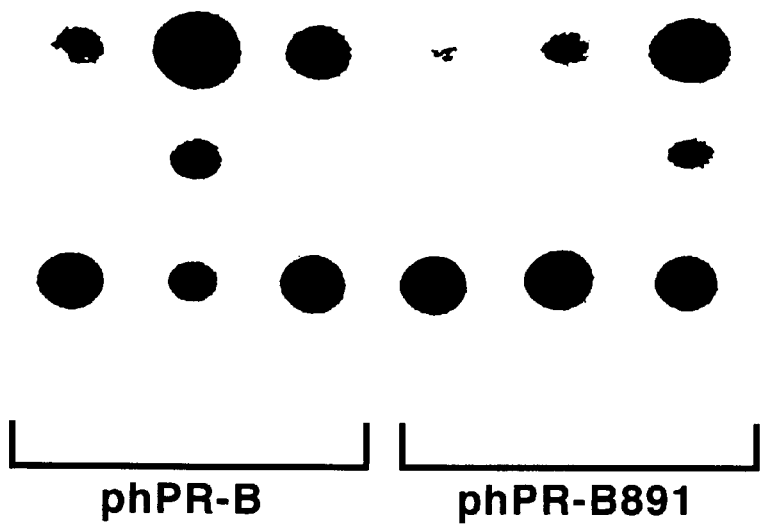

Cell-type specific factors can influence the activity of the transactivating domains of steroid receptors. In order to evaluate this possibility, wild type and mutant receptors were transfected into CV-1 cells. Similar results were obtained, i.e., progesterone activated the wild type receptor while RU38486 activated 891 mutant receptor (FIG. 6B).

The protein synthesized from phPR-B891 plasmid was of the correct molecular weight in mammalian cells. The mutant receptor was transfected into COSM6 cells. Western analysis on cell extracts showed that the 891 mutant was synthesized, as expected, as a protein of 109 kDa, which corresponds to a protein 42 amino acids shorter than the wild type hPR. Thus, RU38486 acts as an agonist of the truncated B-receptor in a yeast reconstituted system and also in mammalian cells. The mechanism of transactivation does not require the C-terminal tail of the mutant receptor and is conserved between the three species tested.

EXAMPLE 16
Chicken Progesterone

Chicken and mammalian progesterone are readily available and both function by binding to the same DNA regulatory sequence. Chicken progesterone, however, binds a different spectrum of ligands, possessing different affinities from those interacting with human progesterone. Thus, the chicken progesterone can be used as a transgene regulator in humans. Further, it can be used to screen for specific ligands which activate chicken progesterone but not endogenous human progesterone. An example of a ligand is 5-alpha-pregnane-3,20-dione (dihydroprogesterone) which binds extremely well to chicken progesterone but does not bind or binds very poorly to human progesterone.

Although the unmodified chicken progesterone is already endowed with a different spectrum of ligand affinity from the human or other mammals and can be used in its native form, it is important to try to select additional mutated progesterones to create a more efficacious receptor. The differences in chicken and human progesterone receptors are due to a few amino acid differences. Thus, other mutations could be artificially introduced. These mutations would enhance the receptor differences. Screening receptor mutations for ligand efficacy produces a variety of receptors in which alterations of affinity occur. The initial screening of progesterone mutants was carried out using intermediate levels of ligands. One mutant had lost progesterone affinity entirely, but bound a synthetic ligand RU38486 with nearly wild-type efficiency. RU38486 is normally considered an antagonist of progesterone function, but had become an agonist when tested using this specific mutant. Because the ligand is synthetic, it does not represent a compound likely to be found in the humans or animals to be treated with gene therapy. Although RU38486 works as an agonist in this case, it is not ideal because of its potential side effects as an anti-glucocorticoid. Further, it also binds to the wild-type human progesterone. Thus it has the undesirable side effect of reproductive and endocrine disfunction.

This approach is not limited to the progesterone receptor, since it is believed that all of the ligand activated transcription factors act through similar mechanisms. One skilled in the art recognizes that similar screening of other members of the steroid superfamily will provide a variety of molecular switches. For example, the compound 1,25-dihydroxy-Vitamin $D_3$ activates the Vitamin D receptor but the compound 24,25-dihydroxy-Vitamin D does not. Mutants of the Vitamin D receptor can be produced which are up-regulated when bound to 24,25-dihydroxy-Vitamin D, but which no longer up-regulates when bound to 1,25-$D_3$.

One skilled in the art recognizes that the ligands are designed to be physiologically tolerated, easily cleared, non-toxic and have specific effects upon the transgene system rather than the entire organism.

EXAMPLE 17

Transgenic Animals

A molecular switch can be used in the production of transgenic animals. A variety of procedures are known for making transgenic animals, including that described in Leder and Stewart, U.S. Pat. No. 4,736,866 issued Apr. 12, 1988 and Palmiter and Bannister Annual Review of Genetics, v. 20, pp. 465–499. For example, the UP-1 molecular switch can be combined with the nucleic acid cassette containing recombinant gene to be expressed. For example, lactoferrin can be placed under the control of a basal thymidine kinase promoter into which has been placed progesterone responsive elements. This vector is introduced into the animal germ lines, along with the vector constitutively expressing the UP-1 receptor. The two vectors can also be combined into one vector. The expression of the recombinant gene in the transgenic animal is turned on or off by administering a pharmacological dose of RU 38486 to the transgenic animal. This hormone serves to specifically activate transcription of the transgene. The dose can be adjusted to regulate the level of expression. One skilled in the art will readily recognize that this protocol can be used for a variety of genes and, thus, it is useful in the regulation of temporal expression of any given gene product in transgenic animals.

EXAMPLE 18

Plants

In this instance, an UP-1 molecular switch can be attached to the nucleic acid cassette containing the gene or recombinant gene to be expressed. For example, the gene for Δ9 desaturase can be placed under the control of a basal 3-phosphoglycerate promoter into which has been placed one or more copies of the progesterone response elements. This vector is then introduced into the plant germ line, along with a vector constitutively expressing the UP-1 receptor. Again, these two vectors can be combined into one vector. At the required time for expression of the nucleic acid cassette, a pharmacological dose of RU 38486 is introduced to activate the transcription. The dose can be adjusted to regulate the level of expression. Thus, one skilled in the art will readily recognize that a variety of genes can be turned on and off in plants by the use of the invention of the present application.

All patents and publications mentioned in this specification are indicative of the levels of those skilled in the art to which the invention pertains. All patents and publications are incorporated herein by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. Transformed cells, vectors, compositions, molecular switches and receptors, along with the methods, procedures, treatments and molecules described herein are presently representative of preferred embodiments, are exemplary and are not intended as limitations on the scope of the invention. Changes therein and other uses will occur to those skilled, in the art which are encompassed within the spirit of the invention as defined by the scope of the claims.

What we claim is:

1. A recombinant virus comprising a nucleic acid cassette that encodes a molecular switch for regulating expression from a promoter transcriptionally linked to a nucleic acid encoding a desired protein, the molecular switch comprising:

(a) a DNA binding domain which binds the promoter;

(b) a mutated steroid hormone receptor superfamily protein ligand binding domain mutated from a naturally occurring steroid hormone superfamily receptor protein ligand binding domain, wherein the mutation confers efficient activation of the molecular switch by an agonist which is an antagonist of the naturally occurring steroid hormone receptor superfamily protein; and (c) a transactivation domain which regulates transcription from the promoter when the mutated ligand binding domain is bound to the agonist and the DNA domain is bound to the promoter.

2. The recombinant virus of claim 1, wherein said mutated steroid hormone receptor superfamily protein is selected from the group consisting of estrogen receptor protein, progesterone receptor protein, glucocorticoid-α receptor protein, glucocorticoid-β receptor protein, mineralocorticoid receptor protein, androgen thyroid hormone receptor protein, retinoic acid receptor protein, retinoid X receptor protein, Vitamin D receptor protein, COUP-TF receptor protein, ecdysone receptor protein, and Nurr-1 receptor protein.

3. A transformed cell line containing the recombinant virus of claim 1.

4. The recombinant virus of claim 1 further comprising a nucleic acid sequence encoding a desired protein wherein the nucleic acid sequence is transcriptionally linked to a promoter that can be regulated by the molecular switch.

5. The recombinant virus of claim 1, wherein said mutated steroid hormone receptor superfamily protein ligand binding domain is mutated by a deletion of carboxy terminal amino acids.

6. The recombinant virus of claim 5, wherein said deletion comprises from about 1 to 120 amino acids.

7. The recombinant virus of claim 5, wherein the ligand binding domain is mutated by a deletion of from about 1 to about 60 carboxy terminal amino acids.

8. The recombinant virus of claim 5, wherein the carboxy terminal deletion comprises a deletion of from about 1 to about 42 carboxy terminal amino acids.

9. A transfected cell containing the recombinant virus of claim 1.

10. The transfected cell of claim 9, wherein the transfected cell is selected from the group consisting of yeast, mammalian and insect cells.

11. A method of determining antagonist activity of a compound for a mutated steroid hormone superfamily receptor, comprising the steps of:

contacting said compound with a transfected cell of claim 9, wherein the transfected cell contains a promoter that can be regulated by the molecular switch; and measuring a transcriptional activity of a nucleic acid transcriptionally linked to the promoter and thereby determining said antagonist activity of said compound for said mutated steroid hormone superfamily receptor.

12. A method of determining agonist activity of a compound for a mutated steroid hormone superfamily receptor comprising the steps of:

contacting said compound with a transfected cell of claim 9, wherein the transfected cell contains a promoter that can be regulated by the molecular switch; and measuring a transcriptional activity of a nucleic acid transcriptionally linked to the promoter and thereby determine said agonist activity of said compound for said mutated steroid hormone superfamily receptor.

13. The method of claim 11 or 12, wherein said mutated steroid hormone superfamily receptor protein is selected from the group consisting of estrogen receptor protein, progesterone receptor protein, glucocorticoid-α receptor protein, glucocorticoid-β receptor protein, mineralocorticoid receptor protein, androgen thyroid hormone receptor protein, retinoic acid receptor protein, retinoid X receptor protein, Vitamin D receptor protein, COUP-TF receptor protein, ecdysone receptor protein, and Nurr-1 receptor protein.

14. The recombinant virus of claim 1, wherein the DNA binding domain is selected from the group consisting of:
 a steroid hormone receptor superfamily protein DNA binding domain,
 a GAL-4 DNA binding domain,
 a virus DNA binding domain,
 an insect DNA binding domain, and
 a non-mammalian DNA binding domain.

15. The recombinant virus of claim 14, wherein the mutated steroid hormone receptor superfamily protein ligand binding domain is mutated to bind a compound selected from the group consisting of non-natural ligands and anti-hormone ligands.

16. The recombinant virus of claim 14, wherein the mutated steroid hormone receptor superfamily protein ligand binding domain binds to and is activated by an agonist compound selected from the group consisting of 5-alpha-pregnane-3,20-dione; 11β-(4-dimethylaminophenyl)-17β-hydroxy-17α-propinyl-4,9-estradiene-3-one; 11β-(4-dimethylaminophenyl)-17α-hydroxy-17β-(3-hydroxypropyl)-13α-methyl-4,9-gonadiene-3-one; 11β-(4-acetylphenyl)-17β-hydroxy-17α-(1-propinyl)-4,9-estradiene-3-one; 11β-(4-dimethylaminophenyl)-17β-hydroxy-17α-(3-hydroxy-1(Z)-propenyl-estra-4,9-diene-3-one; (7β,11β,17β)-11-(4-dimethylaminophenyl)-7-methyl-4',5'-dihydrospiro(ester-4,9-diene-17,2'(3'H)-furan)-3-one; and (11β, 14β,17α)-4',5'-dihydro-11-(4-dimethylaminophenyl)-(spiroestra-4,9diene-17,2'(3'h)-furan)-3-one.

17. The recombinant virus of claim 9, wherein the steroid hormone receptor superfamily protein is selected from the group consisting of estrogen receptor protein, progesterone receptor protein, androgen receptor protein, Vitamin D receptor protein, COUP-TF receptor protein, cis-retinoic acid receptor protein, Nurr-1 receptor protein, thyroid hormone receptor protein, mineralocorticoid receptor protein, glucocorticoid-α receptor protein, and glucocorticoid-β receptor protein.

18. The recombinant virus of claim 9, wherein the DNA binding domain is a GAL-4 DNA binding.

19. The recombinant virus of claim 14, wherein the transactivation domain is selected from the group consisting of: VP-16, TAF-1, TAF-2, TAU-1, and TAU-2.

20. The recombinant virus of claim 9, wherein the mutated steroid hormone receptor superfamily protein ligand binding domain is a mutated steroid hormone superfamily receptor protein ligand binding domain which binds non-natural ligands.

21. The recombinant virus of claim 14, wherein the mutated steroid hormone receptor superfamily protein ligand binding domain is an ecdysone receptor protein ligand binding domain.

22. The recombinant virus of claim 9, wherein said molecular switch is tissue specific.

23. The recombinant virus of claim 22, wherein the tissue specificity is determined by said transactivation domain.

24. The recombinant virus of claim 22, wherein the tissue specificity is determined by the ligand which binds to the ligand binding domain.

25. The recombinant virus of claim 22, further comprising the addition of a tissue-specific nucleic acid cis-element to the nucleic acid encoding the molecular switch.

26. The recombinant virus of claim 1, wherein the transactivation domain is selected from the group consisting of: VP-16, TAF-1, TAF-2, TAU-1, and TAU-2.

27. The recombinant virus of claim 26, wherein the DNA binding domain is selected from the group consisting of: a GAL-4 DNA binding domain, a virus DNA binding domain, an insect DNA binding domain, and a non-mammalian DNA binding domain.

28. A composition of matter comprising a nucleic acid cassette encoding a molecular switch, wherein said cassette is positionally and sequentially oriented in a viral vector such that a nucleic acid in the cassette is transcribed and translated in a target cell, the switch comprising: a modified steroid receptor protein, the receptor protein including a natural steroid receptor DNA binding domain linked to a modified ligand binding domain comprising a carboxyl terminal deletion; wherein said deletion confers efficient activation of the molecular switch by an agonist which is an antagonist of the naturally occurring steroid receptor protein.

29. A recombinant virus containing a nucleic acid cassette encoding a molecular switch, the switch comprising: a VP-16 transactivation region, a GAL-4 DNA binding domain, and a modified steroid hormone superfamily receptor ligand binding domain comprising a carboxyl terminal deletion.

30. A recombinant virus containing a nucleic acid cassette encoding a molecular switch, the switch comprising: a TAF-1 transactivation region, a GAL-4 DNA binding domain, and a modified steroid hormone superfamily receptor ligand binding domain comprising a carboxyl terminal deletion.

31. The recombinant virus of claim 29 or 30, wherein the mutated steroid hormone receptor superfamily protein ligand binding domain binds a compound selected from the group consisting of 5-alpha-pregnane-3,20-dione; 11β-(4-dimethylaminophenyl)-17β-hydroxy-17α-propinyl-4,9-estradiene-3-one; 11β-(4-dimethylaminophenyl)-17α-hydroxy-17β-(3-hydroxypropyl)-13α-methyl-4,9-gonadiene-3-one; 11β-(4-acetylphenyl)-17β-hydroxy-17α-(1-propinyl)-4,9-estradiene-3-one; 11β-(4-dimethylaminophenyl)-17β-hydroxy-17α-(3-hydroxy-1(Z)-propenyl-estra-4,9-diene-3-one; (7β,11β,17β)-11-(4-dimethylaminophenyl)-7-methyl-4',5'-dihydrospiro(ester-4,9-diene17,2'(3'H)-furan)-3-one; and (11β, 14β,17α)-4',5'-dihydro-11-(4-dimethylaminophenyl)-(spiroestra-4,9diene-17,2'(3'h)-furan)-3-one.

32. A composition of matter comprising a molecular switch linked to a nucleic acid cassette, wherein a promoter in the cassette/molecular switch complex contains steroid response elements and wherein the cassette/molecular switch complex is positionally and sequentially oriented in a viral vector such that a nucleic acid in the cassette is transcribed and translated in a target cell, the switch comprising: a modified steroid receptor, said receptor including a natural steroid receptor DNA binding domain linked to a modified ligand binding domain comprising a carboxyl terminal deletion; wherein said deletion confers efficient activation of the molecular switch by an agonist which is an antagonist of the naturally occurring steroid receptor protein.

* * * * *